(12) United States Patent
Shelton, IV et al.

(10) Patent No.: US 11,786,240 B2
(45) Date of Patent: Oct. 17, 2023

(54) USING SMART PACKAGING IN ADJUSTING USE OF TISSUE ADJUNCTS

(71) Applicant: Cilag GmbH International, Zug (CH)

(72) Inventors: Frederick E. Shelton, IV, Hillsboro, OH (US); Michael J. Vendely, Lebanon, OH (US); Shane R. Adams, Lebanon, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 99 days.

(21) Appl. No.: 17/216,953

(22) Filed: Mar. 30, 2021

(65) Prior Publication Data

US 2022/0313245 A1 Oct. 6, 2022

(51) Int. Cl.
| | | |
|---|---|---|
| *A61B 17/072* | (2006.01) | |
| *A61B 17/068* | (2006.01) | |
| *A61B 90/00* | (2016.01) | |
| *A61B 17/00* | (2006.01) | |
| *A61B 17/29* | (2006.01) | |

(52) U.S. Cl.
CPC .... *A61B 17/0686* (2013.01); *A61B 17/07207* (2013.01); *A61B 17/07292* (2013.01); *A61B 90/08* (2016.02); *A61B 17/072* (2013.01); *A61B 2017/00004* (2013.01); *A61B 2017/00017* (2013.01); *A61B 2017/0688* (2013.01); *A61B 2017/2927* (2013.01); *A61B 2090/0807* (2016.02)

(58) Field of Classification Search
CPC . A61B 17/068; A61B 17/0686; A61B 17/072; A61B 17/07207; A61B 17/07292; A61B 17/115; A61B 2017/00004; A61B 2017/00017; A61B 2017/00221; A61B 2017/07214; A61B 2017/07271; A61B 2017/2919; A61B 2017/2927; A61B 34/20; A61B 34/30; A61B 90/08; A61B 2090/0807; A61B 2090/0808
USPC ..... 227/19, 175.2, 176.1, 175.1; 606/1, 139, 606/219
See application file for complete search history.

(56) References Cited

U.S. PATENT DOCUMENTS

| | | | |
|---|---|---|---|
| 5,711,960 | A | 1/1998 | Shikinami |
| 5,833,695 | A | 11/1998 | Yoon |

(Continued)

FOREIGN PATENT DOCUMENTS

| | | |
|---|---|---|
| EP | 2113206 A2 | 11/2009 |
| EP | 2333701 A1 | 6/2011 |

(Continued)

OTHER PUBLICATIONS

Maurus et al., "Bioabsorbable Implant Material Review," Operative Techniques in Sports Medicine, 12:158-160, 2004.

(Continued)

*Primary Examiner* — Scott A Smith
(74) *Attorney, Agent, or Firm* — Mintz Levin Cohn Ferris Glovsky and Popeo, P.C.

(57) ABSTRACT

In general, systems and methods described herein include active or passive sensing mechanisms, such as sensors, that can monitor at least one exposure condition of an adjunct and any medicant(s) retained therein. In some instances, the active or passive sensing mechanisms can also track the extent of the adjunct's and medicant(s)'s exposure, e.g., frequency, intensity, and/or duration).

20 Claims, 16 Drawing Sheets

(56) References Cited

U.S. PATENT DOCUMENTS

| | | | |
|---|---|---|---|
| 6,029,671 A | 2/2000 | Stevens et al. | |
| 7,143,925 B2 | 12/2006 | Shelton, IV et al. | |
| 7,601,118 B2 | 10/2009 | Smith et al. | |
| 8,062,330 B2 | 11/2011 | Prommersberger et al. | |
| 8,317,070 B2 | 11/2012 | Hueil et al. | |
| 8,393,514 B2 | 3/2013 | Shelton, IV et al. | |
| 8,864,007 B2 | 10/2014 | Widenhouse et al. | |
| 9,084,602 B2 | 7/2015 | Gleiman | |
| 9,232,941 B2 | 1/2016 | Mandakolathur et al. | |
| 9,272,406 B2 | 3/2016 | Aronhalt et al. | |
| 9,282,962 B2 | 3/2016 | Schmid et al. | |
| 9,480,476 B2 | 11/2016 | Aldridge et al. | |
| 9,681,936 B2 | 6/2017 | Hodgkinson et al. | |
| 9,913,642 B2 | 3/2018 | Leimbach et al. | |
| 9,999,408 B2 | 6/2018 | Boudreaux et al. | |
| 10,111,661 B2 | 10/2018 | Widenhouse et al. | |
| 10,136,890 B2 | 11/2018 | Shelton, IV et al. | |
| 10,166,023 B2 | 1/2019 | Vendely et al. | |
| 10,172,611 B2 | 1/2019 | Shelton, IV et al. | |
| 10,172,617 B2 | 1/2019 | Shelton, IV et al. | |
| 10,172,618 B2 | 1/2019 | Shelton, IV et al. | |
| 10,251,649 B2* | 4/2019 | Schellin | A61B 50/30 |
| 10,258,332 B2 | 4/2019 | Schmid et al. | |
| 10,265,091 B2 | 4/2019 | Nativ et al. | |
| 10,285,692 B2 | 5/2019 | Widenhouse et al. | |
| 10,349,939 B2 | 7/2019 | Shelton, IV et al. | |
| 10,368,869 B2 | 8/2019 | Olson et al. | |
| 10,433,846 B2 | 10/2019 | Vendely et al. | |
| 10,517,592 B2 | 12/2019 | Shelton, IV et al. | |
| 10,548,593 B2 | 2/2020 | Shelton, IV et al. | |
| 10,568,621 B2 | 2/2020 | Shelton, IV et al. | |
| 10,569,071 B2 | 2/2020 | Harris et al. | |
| 10,588,623 B2 | 3/2020 | Schmid et al. | |
| 10,772,732 B1 | 9/2020 | Miller et al. | |
| 10,939,911 B2 | 3/2021 | Huitema et al. | |
| 11,116,505 B2* | 9/2021 | Vendely | A61B 17/07207 |
| 11,224,423 B2* | 1/2022 | Shelton, IV | A61B 17/072 |
| 11,291,449 B2* | 4/2022 | Swensgard | A61B 17/32 |
| 11,406,377 B2* | 8/2022 | Schmid | A61B 17/0682 |
| 11,504,125 B2 | 11/2022 | Shelton, IV et al. | |
| 11,602,341 B2 | 3/2023 | Shelton, IV et al. | |
| 11,627,961 B2 | 4/2023 | Shelton, IV et al. | |
| 2002/0014951 A1 | 2/2002 | Kramer et al. | |
| 2004/0101546 A1 | 5/2004 | Gorman et al. | |
| 2004/0101548 A1 | 5/2004 | Pendharkar | |
| 2005/0070929 A1* | 3/2005 | Dalessandro | A61B 17/07292 |
| | | | 606/151 |
| 2007/0021760 A1 | 1/2007 | Kelleher | |
| 2007/0034669 A1 | 2/2007 | de la Torre et al. | |
| 2007/0179528 A1 | 8/2007 | Soltz et al. | |
| 2007/0251835 A1 | 11/2007 | Mika et al. | |
| 2008/0051866 A1 | 2/2008 | Chen et al. | |
| 2009/0093550 A1 | 4/2009 | Rolfes et al. | |
| 2009/0123517 A1 | 5/2009 | Flanagan et al. | |
| 2009/0206142 A1* | 8/2009 | Huitema | A61B 17/07207 |
| | | | 227/176.1 |
| 2009/0209031 A1 | 8/2009 | Stopek | |
| 2010/0331880 A1 | 12/2010 | Stopek | |
| 2012/0080491 A1 | 4/2012 | Shelton, IV et al. | |
| 2012/0100200 A1 | 4/2012 | Belcheva et al. | |
| 2012/0241491 A1 | 9/2012 | Aldridge et al. | |
| 2012/0241498 A1 | 9/2012 | Gonzalez et al. | |
| 2012/0289979 A1* | 11/2012 | Eskaros | A61B 17/07292 |
| | | | 606/151 |
| 2013/0146643 A1 | 6/2013 | Schmid et al. | |
| 2013/0172929 A1 | 7/2013 | Hess et al. | |
| 2013/0221065 A1 | 8/2013 | Aronhalt et al. | |
| 2013/0256377 A1 | 10/2013 | Schmid et al. | |
| 2014/0166726 A1 | 6/2014 | Schellin et al. | |
| 2014/0205637 A1 | 7/2014 | Widenhouse et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0136831 A1 | 5/2015 | Baxter, III et al. | |
| 2015/0196296 A1 | 7/2015 | Swayze et al. | |
| 2015/0238191 A1 | 8/2015 | Schellin et al. | |
| 2015/0297236 A1 | 10/2015 | Harris et al. | |
| 2015/0351761 A1 | 12/2015 | Shelton, IV et al. | |
| 2015/0351764 A1 | 12/2015 | Shelton, IV | |
| 2016/0100839 A1 | 4/2016 | Marczyk et al. | |
| 2016/0106427 A1 | 4/2016 | Shelton, IV et al. | |
| 2016/0345976 A1 | 12/2016 | Gonzalez et al. | |
| 2017/0049448 A1 | 2/2017 | Widenhouse et al. | |
| 2017/0055986 A1 | 3/2017 | Harris et al. | |
| 2017/0055992 A1 | 3/2017 | Widenhouse et al. | |
| 2017/0055994 A1 | 3/2017 | Vendely et al. | |
| 2017/0056018 A1 | 3/2017 | Zeiner et al. | |
| 2017/0056567 A1 | 3/2017 | Harris et al. | |
| 2017/0119391 A1* | 5/2017 | Schellin | A61B 50/30 |
| 2017/0235613 A1 | 8/2017 | Smola et al. | |
| 2017/0281181 A1 | 10/2017 | Matonick et al. | |
| 2017/0296213 A1 | 10/2017 | Swensgard et al. | |
| 2018/0085124 A1 | 3/2018 | Nativ et al. | |
| 2018/0235613 A1 | 8/2018 | Shelton, IV et al. | |
| 2018/0235616 A1 | 8/2018 | Shelton, IV et al. | |
| 2018/0235625 A1 | 8/2018 | Shelton, IV et al. | |
| 2018/0353174 A1 | 12/2018 | Widenhouse et al. | |
| 2018/0353175 A1 | 12/2018 | Widenhouse et al. | |
| 2018/0353659 A1 | 12/2018 | Widenhouse et al. | |
| 2019/0200844 A1 | 7/2019 | Shelton, IV et al. | |
| 2019/0200981 A1 | 7/2019 | Harris et al. | |
| 2019/0201140 A1 | 7/2019 | Yates et al. | |
| 2019/0206004 A1 | 7/2019 | Shelton, IV et al. | |
| 2019/0206562 A1 | 7/2019 | Shelton, IV et al. | |
| 2019/0254654 A1 | 8/2019 | Shelton, IV et al. | |
| 2019/0254655 A1 | 8/2019 | Shelton, IV et al. | |
| 2019/0254661 A1 | 8/2019 | Shelton, IV et al. | |
| 2019/0254670 A1 | 8/2019 | Shelton, IV et al. | |
| 2019/0290267 A1 | 9/2019 | Baxter, III et al. | |
| 2019/0328390 A1 | 10/2019 | Harris et al. | |
| 2019/0344064 A1 | 11/2019 | Buchanan | |
| 2020/0205825 A1 | 7/2020 | Vendely et al. | |
| 2020/0238244 A1 | 7/2020 | Tchakalova et al. | |
| 2021/0077094 A1 | 3/2021 | Harris et al. | |
| 2021/0077109 A1 | 3/2021 | Harris et al. | |
| 2021/0346015 A1* | 11/2021 | Krulevitch | A61B 17/0686 |
| 2022/0313145 A1 | 10/2022 | Shelton, IV et al. | |
| 2022/0313245 A1* | 10/2022 | Shelton, IV | A61B 90/08 |
| 2022/0313246 A1 | 10/2022 | Shelton, IV et al. | |
| 2022/0313247 A1 | 10/2022 | Shelton, IV et al. | |
| 2022/0313248 A1 | 10/2022 | Shelton, IV et al. | |
| 2022/0313255 A1* | 10/2022 | Shelton, IV | A61B 17/07292 |
| 2022/0313256 A1 | 10/2022 | Shelton, IV et al. | |
| 2022/0313257 A1 | 10/2022 | Shelton, IV et al. | |
| 2022/0313258 A1 | 10/2022 | Shelton, IV et al. | |
| 2022/0313259 A1 | 10/2022 | Shelton, IV et al. | |
| 2022/0313260 A1 | 10/2022 | Shelton, IV et al. | |
| 2022/0313261 A1 | 10/2022 | Shelton, IV et al. | |
| 2022/0313262 A1 | 10/2022 | Shelton, IV et al. | |
| 2022/0313874 A1 | 10/2022 | Shelton, IV et al. | |

FOREIGN PATENT DOCUMENTS

| | | |
|---|---|---|
| EP | 2395333 A1 | 12/2011 |
| EP | 2604196 A2 | 6/2013 |
| EP | 2628491 A2 | 8/2013 |
| EP | 3132811 A1 | 2/2017 |
| EP | 3162297 A1 | 5/2017 |
| EP | 3530199 A2 | 8/2019 |
| EP | 3756612 A2 | 12/2020 |
| EP | 3782558 A1 | 2/2021 |
| EP | 3791804 A2 | 3/2021 |
| EP | 3791809 A1 | 3/2021 |
| WO | WO-9824048 A1 | 6/1998 |
| WO | WO-2006044490 A2 | 4/2006 |
| WO | WO-2006068999 A2 | 6/2006 |
| WO | WO-2015187793 A1 | 12/2015 |

(56) References Cited

FOREIGN PATENT DOCUMENTS

| WO | WO-2020021433 A1 | 1/2020 |
|---|---|---|
| WO | WO-2022079516 A1 | 4/2022 |

OTHER PUBLICATIONS

What are Stents?, NIH National Heart, Lung, and Blood Institute, (https://www.nhlbi.nih.gov/health/stents#:-:text=A%stent%20is%20a%20small,heart%20with%20oxygen%2Drich%20blood), Mar. 24, 2022.
U.S. Appl. No. 17/217,252, filed Mar. 30, 2021, Method for Treating Tissue.
U.S. Appl. No. 17/216,977, filed Mar. 30, 2021, Compressible Adjuncts With Fluid Control Features.
U.S. Appl. No. 17/216,978, filed Mar. 30, 2021, Compressible Adjuncts With Drug Release Features.
U.S. Appl. No. 17/216,982, filed Mar. 30, 2021, Compressible Adjuncts With Drug Release Features.
U.S. Appl. No. 17/216,985, filed Mar. 30, 2021, Compressible Adjuncts With Drug Dosage Control Features.
U.S. Appl. No. 17/216,994, filed Mar. 30, 2021, Compressible Adjuncts With Different Behavioral Zones.
U.S. Appl. No. 17/216,914, filed Mar. 30, 2021, Smart Packaging for Tissue Adjuncts.
U.S. Appl. No. 17/216,946, filed Mar. 30, 2021, Passively Powered Packaging for Tissue Adjuncts.
U.S. Appl. No. 17/216,960, filed Mar. 30, 2021, Monitoring Healing After Tissue Adjunct Implantation.
U.S. Appl. No. 17/216,578, filed Mar. 30, 2021, Implantable Adjuncts Having Adjustable Degradation Profile.
U.S. Appl. No. 17/217,680, filed Mar. 30, 2021, Compressible Adjuncts With Healing-Dependent Degradation Profile.
U.S. Appl. No. 17/217,736, filed Mar. 30, 2021, Tissue Thickness Compensating Adjuncts Having Regions of Differential Expansion.
U.S. Appl. No. 17/217,784, filed Mar. 30, 2021, Composite Adjuncts That Degrade Through Multiple Different Mechanisms.
International Patent Application No. PCT/IB2020/060710 entitled "Drug Delivery Device Sensing Modules", filed on Nov. 13, 2020, 100 pages.
U.S. Appl. No. 17/022,520 entitled "Method of Applying Buttress to End Effector of Surgical Stapler", filed Sep. 16, 2020, 226 pages.
U.S. Appl. No. 17/068,857 entitled "Adaptive Responses From Smart Packaging of Drug Delivery Absorbable Adjuncts", filed Oct. 13, 2020, 97 pages.
Agren et al. (Jul. 2006) "Action of Matrix Metalloproteinases at Restricted Sites in Colon Anastomosis Repair: An Immunohistochemical and Biochemical Study", Surgery, 140(1):72-82.
Aslanian et al. (Mar.-Apr. 1984) "Dietary Intake and Urinary Excretion of Various Mineral Substances in Patients with Hypertension and Ischemic Heart Disease", Vopr Pitan, (2):16-9(English Abstract).
Bezwada Rao S. (2008) "Controlled Release of Drugs from Novel Absorbable Oligomers and Polymes", White Paper, Bezwada Biomedical, 7 pages.
Bezwada Rao S. (2008) "Functionalized Triclosan for Controlled Release Applications", White Paper, AP Bezwada Biomedical, 6 pages.
Bezwada Rao S. (2010) "Nitric Oxide and Drug Releasing Hydrolysable Macromes Oligomers and Polymes", Chapter 11 of Biomaterials, ACS Symposium Series, American Chemical Society: Washington, DC, 24 pages.
Bezwada Rao S. (Mar. 2009) "Nitric Oxide and Drug Releasing Hydrolysable Macromes, Oligomers and AR Polymers", White Paper, Bezwada Biomedical, 9 pages.
Bosmans et al. (2015) "Colorectal Anastomotic Healing: Why the Biological Processes that Lead to Anastomotic Leakage Should Be Revealed Prior to Conducting Intervention Studies", BMC Gastroenterology, 15:180(6 pages).
Broughton et al. (Jun. 2006) "The Basic Science of Wound Healing", Plastic and Reconstructive Surgery, 117(7 Suppl):12S-34S.
Casalani et al. (Oct. 11, 2019) "A Perspective on Polylactic Acid-Based Polymers Use for Nanoparticles Synthesis and Applications", Frontiers in Bioengineering and Biotechnology, 17(259):1-16.
De Hingh et al. (Jun. 21, 2002) "The Matrix Metalloproteinase Inhibitor BB-94 Improves the Strength of Intestinal Anastomoses in the Rat", International Journal of Colorectal Disease, 17(5):348-354.
Fatouros et al. (Oct. 1999) "Influence of Growth Factors Erythropoietin and Granulocyte Macrophage Colony Stimulating Factor on Mechanical Strength and Healing of Colonic Anastomoses in Rats", The European Journal of Surgery, 165(10):986-992.
Gibson et al. (Nov. 2009) "MMPs Made Easy", Wounds International, 1(1):1-6.
Hayden et al. (Jun. 15, 2011) "The Role of Matrix Metalloproteinases in Intestinal Epithelial Wound Healing During Normal and Inflammatory States", Journal of Surgical Research, 168(2):315-324.
Holte et al. (Jun. 2009) "Cyclo-oxygenase 2 Inhibitors and the Risk of Anastomotic Leakage After Fast-Track Colonic Surgery", British Journal of Surgery, 96(6):650-654.
Kaemmer et al. (Oct. 2010) "Erythropoietin (EPO) Influences Colonic Anastomotic Healing in a Rat Model by Modulating Collagen Metabolism", Journal of Surgical Research, 163(2):e67-e72.
Kiyama et al. (Sep. 2002) "Tacrolimus Enhances Colon Anastomotic Healing in Rats", Wound Repair and Regeneration, 10(5):308-313.
Klein et al. (Jan. 2011) "Effect of Diclofenac on Cyclooxygenase-2 Levels and Early Breaking Strength of Experimental Colonic Anastomoses and Skin Incisions", European Surgical Research, 46(1):26-31.
Klein et al. (Jul. 18, 2010 "Physiology and Pathophysiology of Matrix Metalloproteases", Amino Acids, 41(2):271-290.
Krarup et al. (Apr. 26, 2013) Expression and Inhibition of Matrix Metalloproteinase (MMP)-8, MMP-9 and MMP-12 in Early Colonic Anastomotic Repair, International Journal of Colorectal Disease, 28(8):1151-1159.
Martens et al. (Dec. 1991) "Postoperative changes in collagen synthesis in intestinal anastomoses of the rat differences between small and large bowel", Gut, 32(12):1482-1487.
Moran et al. (May 15, 2007) "The Effect of Erythropoietin on Healing of Obstructive vs Nonobstructive Left Colonic Anastomosis: An Experimental Study", World Journal of Emergency Surgery, 2:13(6 pages).
Munireddy et al. (Dec. 2010) "Intra-abdominal Healing: Gastrointestinal Tract and Adhesions", Surgical Clinics of North America, 90(6):1227-1236(10 pages).
Øines et al. (Sep. 21, 2014) "Pharmacological Interventions for Improved Colonic Anastomotic Healing: A MetaAnalysis", World Journal of Gastroenterology, 20(35): 12637-12648.
Raptis et al. (Mar. 2012) "The Effects of Tacrolimus on Colonic Anastomotic Healing in Rats", International Journal of Colorectal Disease, 27(3):299-308.
Savage et al. (Aug. 1997) "Role of Matrix Metalloproteinases in Healing of Colonic Anastomosis", Diseases of the Colon & Rectum, 40(8):962-970.
Siemonsma et al. (Mar. 1, 2003) "Doxycycline Improves Wound Strength After Intestinal Anastomosis in the Rat", Surgery, 133(3):268-276.
Thompson et al. (2006) "Clinical Review: Healing in Gastrointestinal Anastomoses, Part I", Microsurgery, 26 (3):131-136.
Vandenbroucke et al. (Dec. 2014) "Is There New Hope for Therapeutic Matrix Metalloproteinase Inhibition?", Nature Reviews Drug Discovery, 13(12):904-927.
Witte et al. (Aug. 2003) "Repair of Full-thickness Bowel Injury", Critical Care Medicine, 31(8 Suppl):S538-S546.
International Search Report and Written Opinion received for PCT Application No. PCT/IB2022/052795, dated Oct. 10, 2022, 19 pages.
International Search Report and Written Opinion received for PCT Application No. PCT/IB2022/052796, dated Oct. 11, 2022, 21 pages.

(56) References Cited

OTHER PUBLICATIONS

International Search Report and Written Opinion received for PCT Application No. PCT/IB2022/052822, dated Oct. 13, 2022, 20 pages.
International Search Report and Written Opinion received for PCT Application No. PCT/IB2022/052798, dated Aug. 18, 2022, 14 pages.
International Search Report and Written Opinion received for PCT Application No. PCT/IB2022/052804, dated Jul. 8, 2022, 16 pages.
International Search Report and Written Opinion received for PCT Application No. PCT/IB2022/052806, dated Jul. 27, 2022, 17 pages.
International Search Report and Written Opinion received for PCT Application No. PCT/IB2022/052807, dated Jul. 7, 2022, 14 pages.
International Search Report and Written Opinion received for PCT Application No. PCT/IB2022/052809, dated Jul. 27, 2022, 17 pages.
International Search Report and Written Opinion received for PCT Application No. PCT/IB2022/052811, dated Jul. 7, 2022, 18 pages.
International Search Report and Written Opinion received for PCT Application No. PCT/IB2022/052813, dated Jul. 27, 2022, 15 pages.
International Search Report and Written Opinion received for PCT Application No. PCT/IB2022/052815, dated Jul. 20, 2022, 13 pages.
International Search Report and Written Opinion received for PCT Application No. PCT/IB2022/052816, dated Jul. 12, 2022, 16 pages.
International Search Report and Written Opinion received for PCT Application No. PCT/IB2022/052818, dated Aug. 10, 2022, 14 pages.
Invitation to Pay Additional Fees received for PCT Application No. PCT/IB2022/052795, dated Jul. 20, 2022, 11 pages.
Invitation to Pay Additional Fees received for PCT Application No. PCT/IB2022/052796, dated Jul. 27, 2022, 13 pages.
Invitation to Pay Additional Fees received for PCT Application No. PCT/IB2022/052822, dated Aug. 12, 2022, 13 pages.

\* cited by examiner

USING SMART PACKAGING IN ADJUSTING USE OF TISSUE ADJUNCTS

FIELD OF THE INVENTION

The present disclosure relates generally to tissue adjuncts and methods of using tissue adjuncts.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling.

It can be beneficial to apply adjuncts to tissue at the surgical site. For example, adjuncts can be used to prevent blood, air, gastrointestinal fluids, and other fluids from seeping through holes formed by the staples. For another example, the adjunct can include a medicant therein that is configured to be released from the adjunct after the adjunct has been applied to tissue. The medicant can be configured to provide one or more benefits for healing, such as encouraging hemostasis, reducing inflammation, and stimulate cell proliferation.

Adjuncts can be absorbable. An adjunct being absorbable allows the adjunct to dissolve or degrade within a patient's body and thus not require additional surgery or other process to remove the adjunct from the patient's body. In instances in which the adjunct contains a medicant, the adjunct being absorbable facilitates automatic release of the medicant from the adjunct as the adjunct dissolves or degrades. However, medicants and/or material forming absorbable adjuncts can be adversely affected by any of a variety of factors between the adjunct being packaged and the adjunct being used. For example, environmental factors may cause a reduction in the medicant's effectiveness and/or may cause the adjunct to begin degrading before being implanted in a patient's body. For another example, a medicant may expire before the adjunct containing the medicant is implanted in a patient's body.

Accordingly, there remains a need for improved adjuncts.

SUMMARY

Various systems and methods of using smart packagings in adjusting use of tissue adjuncts are provided.

In one aspect, a surgical system is provided that in one embodiment includes a bioabsorbable adjunct configured to be implanted in a body of a patient using a surgical stapler, a medicant releasably retained by the adjunct and configured to be released from the adjunct into the body of the patient, a packaging unit packaging the adjunct and the medicant, and a sensor configured to, with the packaging unit packaging the adjunct and the medicant, gather data regarding an exposure condition of at least one of the adjunct and the medicant. The exposure condition is a condition that affects performance of at least one of the adjunct in the body of the patient and the medicant in the body of the patient. The surgical system also includes a processor configured to receive the data gathered by the sensor, determine a recommendation of use of the adjunct and the medicant in a surgical procedure based on the received data and on a requirement of the surgical procedure, and cause notice of the recommendation to be provided to a medical practitioner associated with the surgical procedure.

The surgical system can have any number of variations. For example, the recommendation can include a recommended shelf-life of the adjunct and the medicant. For another example, the recommendation can include a recommended indication of the adjunct and the medicant. For yet another example, the recommendation can include a recommended contraindication of the adjunct and the medicant. For still another example, the recommendation can include a recommended shelf-life of the adjunct and the medicant that is based at least on the gathered data regarding the exposure condition, the recommendation can include at least one of a recommended indication and a recommended contraindication of the adjunct and the medicant, and the at least one of the recommended indication and the recommended contraindication can be based at least on the requirement of the surgical procedure. For another example, the recommendation can include a recommended time after opening of the packaging unit within which the adjunct should be implanted in the body of the patient in the surgical procedure. For still another example, the requirement of the surgical procedure can be specific to a threshold adjunct durability for a type of the surgical procedure, and determining the recommendation can include comparing the threshold adjunct durability with a durability of the adjunct as indicated by the gathered data regarding the exposure condition. For yet another example, the environmental condition can include at least one of light and temperature. For still another example, the environmental condition can include at least one of humidity, oxygen, time, light, vibration, and atmospheric pressure. For another example, the packaging unit can include the sensor. For yet another example, a surgical hub that is external to the packaging unit can include the processor. For still another example, the processor can be configured to, based the received data, set an operational parameter of the surgical stapler.

In another aspect, a surgical method is provided that in one embodiment includes receiving at a computer system external to a packaging unit, from a communications interface of the packaging unit packaging a bioabsorbable adjunct that releasably retains a medicant therein and that is configured to be implanted using a surgical stapler, data gathered by a sensor of the packaging unit indicative of an exposure condition of the packaging unit. The exposure condition is a condition that affects performance of at least one of the adjunct in a patient and the medicant in the patient. The surgical method also includes determining, at the computer system, a recommendation of use of the adjunct and the medicant in a surgical procedure based on the received data indicative of the exposure condition, and a requirement of the surgical procedure. The surgical method also includes providing notice of the recommendation to a medical practitioner associated with the surgical procedure.

The surgical method can vary in any number of ways. For example, the recommendation can include a recommended shelf-life of the adjunct and the medicant. For another example, the recommendation can include a recommended indication of the adjunct and the medicant. For yet another example, the recommendation can include a recommended contraindication of the adjunct and the medicant. For still another example, the recommendation can include a recommended time after opening of the packaging unit within which the adjunct should be implanted in the body of the patient in the surgical procedure. For another example, the requirement of the surgical procedure can be specific to a threshold adjunct durability for a type of the surgical procedure, and determining the recommendation can include comparing the threshold adjunct durability with a durability of the adjunct as indicated by the gathered data regarding the exposure condition. For still another example, the requirement of the surgical procedure can be specific to at least one of a patient on which the surgical procedure is to be performed and a surgeon to perform the surgical procedure. For another example, the surgical method can also include gathering the data, using the sensor of the packaging unit, prior to opening of the packaging unit, and transmitting, using a communications interface of the packaging unit, the data to be received at the computer system. For yet another example, the environmental condition can include at least one of light, temperature, humidity, oxygen, time, light, vibration, and atmospheric pressure. For still another example, the surgical method can also include the processor setting, based the received data, an operational parameter of the surgical stapler.

BRIEF DESCRIPTION OF THE DRAWINGS

This invention will be more fully understood from the following detailed description taken in conjunction with the accompanying drawings, in which.

DETAILED DESCRIPTION

Figure 1:
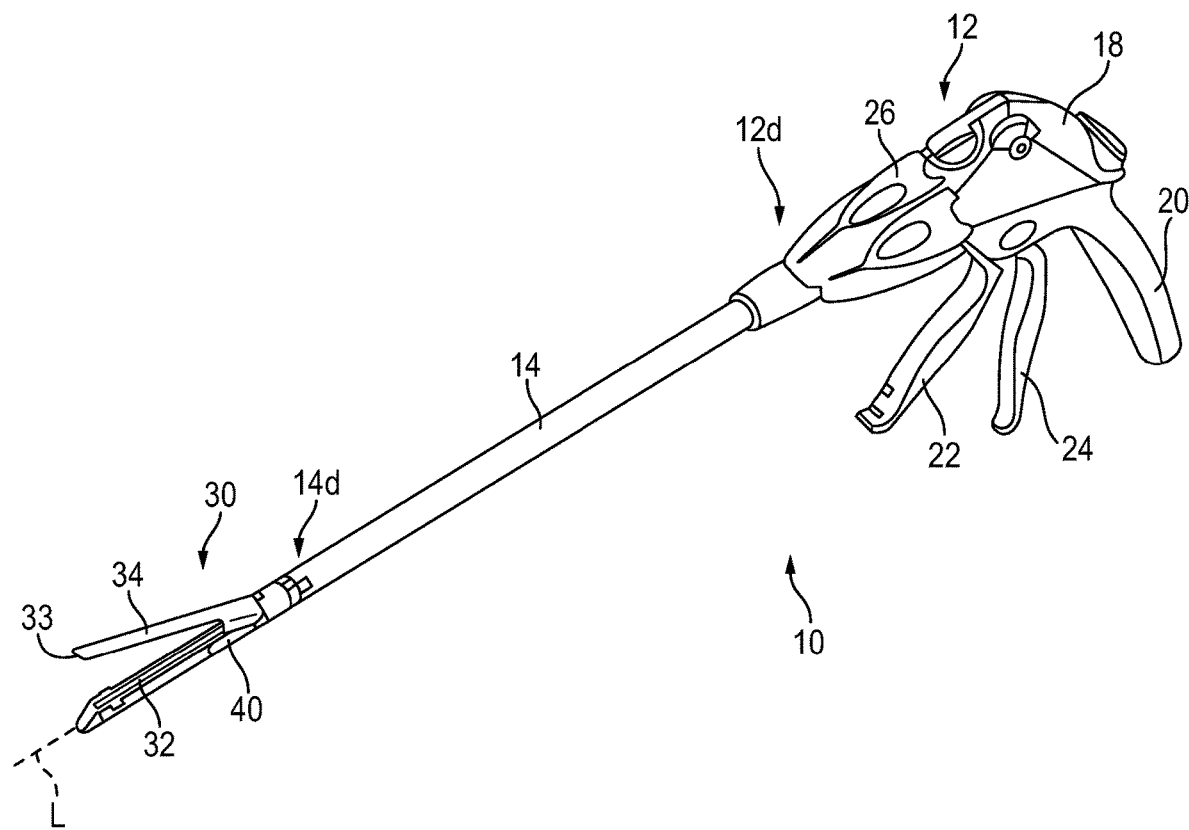
FIG. 1 is a perspective view of one exemplary embodiment of a conventional surgical stapling and severing instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, referred to herein as "adjuncts," in conjunction with surgical instruments to help improve surgical procedures. "Adjuncts" are also referred to herein as "adjunct materials." While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing, and/or is experiencing another tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissue's movement around these puncture sites can minimize the size the holes may grow to under tension. In some instances, the adjunct(s) can be configured to wick or absorb beneficial fluids, e.g., sealants, blood, glues, and the like, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts.

In other embodiments, the adjunct(s) can be used with surgical instruments that are configured to seal tissue without using staples (e.g., by using energy, such as RF or ultrasound), for example, as described in U.S. Pat. No. 10,172,611, which is incorporated by reference herein in its entirety.

In some instances, the adjunct(s) can be configured to compensate for variations in tissue thickness when the adjunct(s) are stapled to tissue. In such instances, the adjunct can be also be referred to as a "tissue thickness compensator." A tissue thickness compensator has an uncompressed (undeformed), or pre-deployed, height that is greater than the height of a staple that is in a formed configuration. Additional details on exemplary tissue thickness compensators can be found in, for example, U.S. Pat. No. 8,864,007, which is incorporated by reference herein in its entirety. A tissue thickness compensator can be attached and released from a staple cartridge in a variety of ways, for example, as described in U.S. Pat. Nos. 9,272,406, and 10,136,890, each of which is incorporated by reference herein in its entirety.

In addition to the disclosures herein, additional details pertaining to the adjunct(s) and other exemplary adjuncts can be found in, for example, U.S. Pat. Nos. 10,172,611 and 10,433,846 and U.S. patent application Ser. No. 17/009,769, filed on Sep. 1, 2020, and entitled "Compressible Non-Fibrous Adjuncts," each of which is incorporated herein by reference in its entirety.

Alternatively or in addition, the adjunct(s) can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

Alternatively or in addition, the adjunct(s) can have medicant(s) thereon and/or therein. The medicant(s) can vary depending on the desired effect of the medicant(s) on the surrounding tissue. As a non-limiting example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As non-limiting examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc. In addition to the disclosures herein, additional details on drug eluting adjuncts can be found in U.S. Pat. Nos. 9,232,941 and 10,569,071, each of which is incorporated herein by reference in its entirety.

Surgical Stapling Instruments

A variety of surgical instruments can be used in conjunction with the adjunct(s) and/or medicant(s) disclosed herein. The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
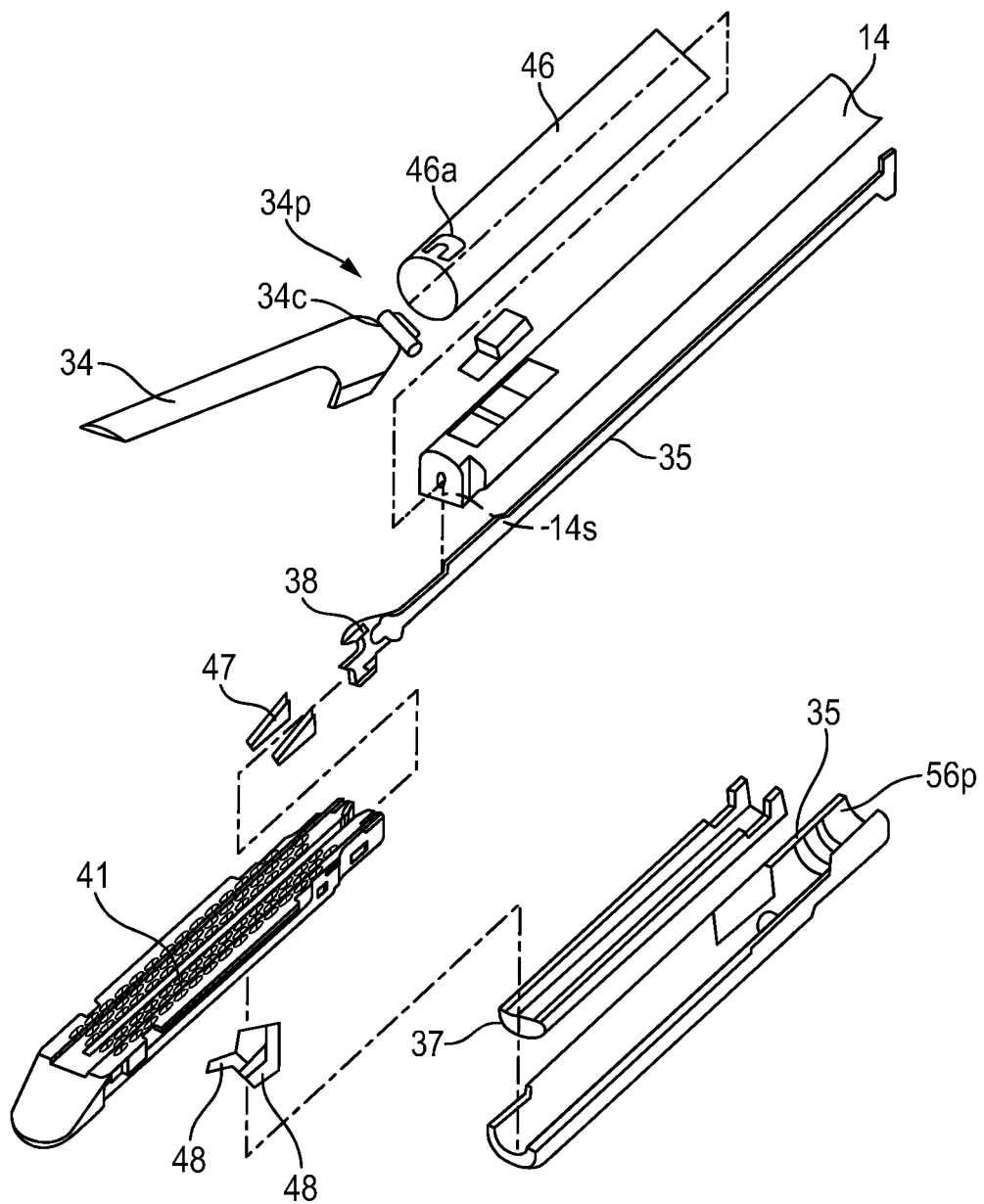
FIG. 2 is a top view of a staple cartridge for use with the surgical stapling and severing instrument of FIG. 1.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
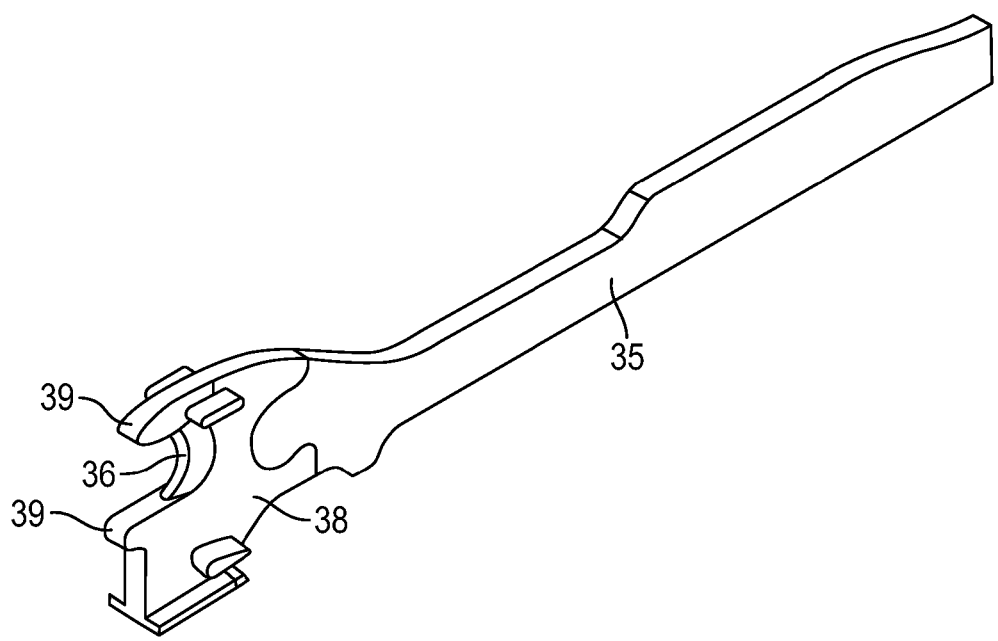
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
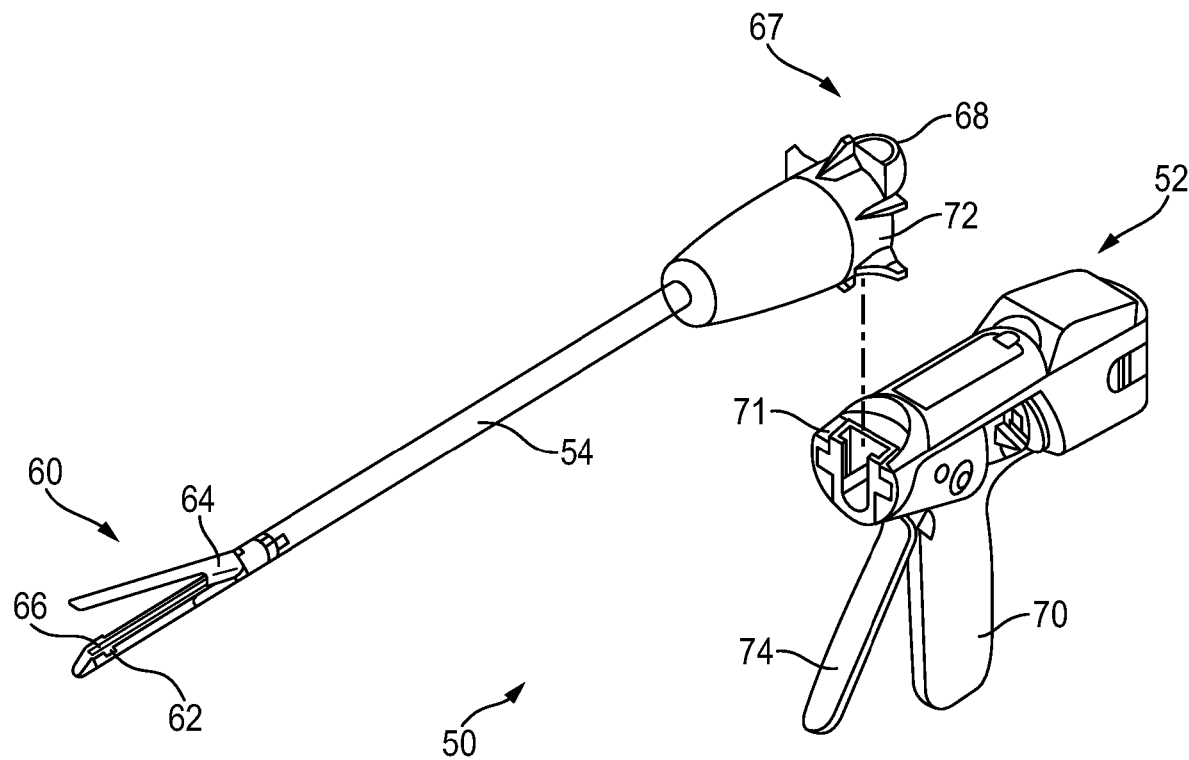
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
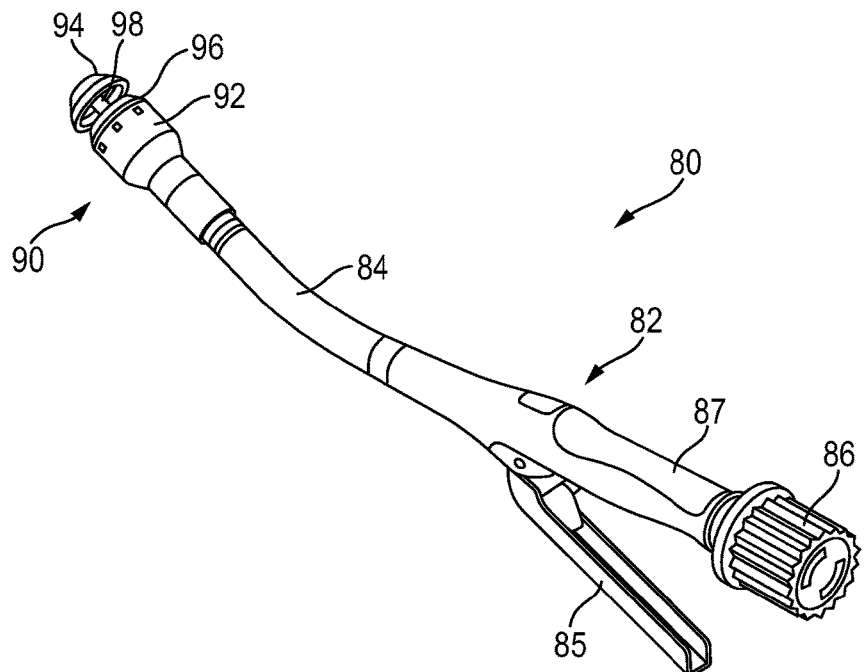
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, e.g., move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are incorporated by reference herein in their entireties.

Implantable Adjuncts

Figure 6:
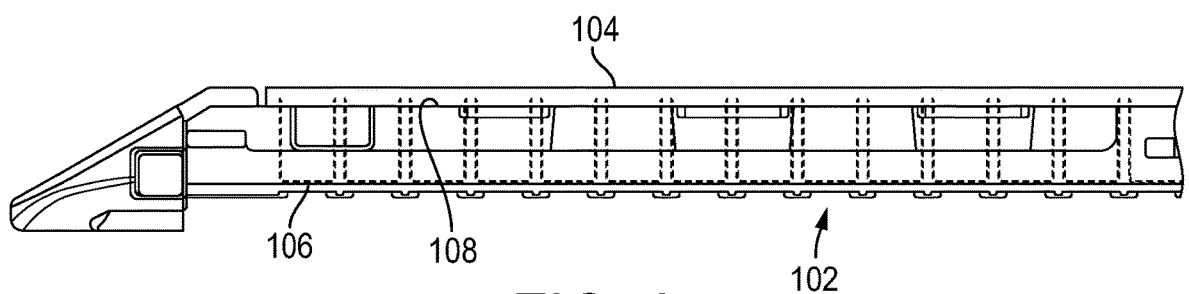
FIG. 6 is a longitudinal cross-sectional view of an exemplary embodiment of a staple cartridge having an exemplary adjunct attached to a top or deck surface thereof.

As indicated above, various implantable adjuncts are provided for use in conjunction with surgical stapling instruments. When used in conjunction with a surgical stapler, the adjunct(s) can be disposed between and/or on jaws of the stapler, incorporated into a staple cartridge disposed in the jaws, or otherwise placed in proximity to the staples. For example, as shown in FIG. 6, an adjunct 104 is positioned against a staple cartridge 102. For sake of simplicity, the adjunct 104 is generally illustrated in FIG. 6, and various structural configurations of the adjunct are described in more detail below. While partially obstructed in FIG. 6, the staple cartridge 102 includes staples 106 that are configured to be deployed into tissue. The staples 106 can have any suitable unformed (pre-deployed) height. For example, the staples 106 can have an unformed height between about 2 mm and 4.8 mm. Prior to deployment, the crowns of the staples can be supported by staple drivers (not shown).

In the illustrated embodiment, the adjunct 104 can be releasably mated to at least a portion of the top surface or deck surface 108 of the staple cartridge 102. In some embodiments, the top surface 108 of the staple cartridge 102 can include one or more surface features. Alternatively, or in addition, one or more adhesives can be used to releasably mate the adjunct to the staple cartridge 102. The one or more surface features and/or the one or more adhesives can be configured to engage the adjunct 104 to avoid undesirable movements of the adjunct 104 relative to the staple cartridge 102 and/or to prevent premature release of the adjunct 104 from the staple cartridge 102. Exemplary surface features are described in U.S. Patent Publication No. 2016/0106427, which is incorporated by reference herein in its entirety. Additional details on adhesives for temporary attachment to instruments and other exemplary adhesives can be found in U.S. Pat. Nos. 9,282,962, 10,172,617, 10,172,618, 10,258, 332, 10,517,592, 10,548,593, 10,568,621, and 10,588,623, each of which is incorporated by reference herein in its entirety. Additional details on attachment methods and other exemplary methods can be found in U.S. Pat. Nos. 10,166, 023 and 10,349,939 and U.S. patent application Ser. No. 17/022,520, filed on Sep. 16, 2020, and entitled "Method of Applying Buttress to End Effector of Surgical Stapler," each of which is incorporated by reference herein in its entirety.

Figure 7:
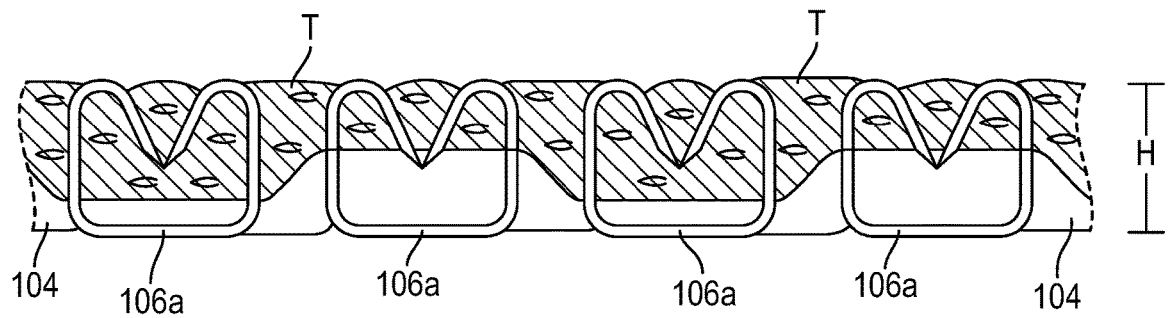
FIG. 7 is a partial-schematic illustrating the adjunct of FIG. 6 in a tissue deployed condition.

In certain instances, the adjunct can be compressible to permit the adjunct to compress to varying heights to thereby compensate for different tissue thickness that are captured within a deployed staple. For example, as illustrated in FIG. 6, the adjunct 104 has an uncompressed (undeformed), or pre-deployed, height and is configured to deform to one of a plurality of compressed (deformed), or deployed, heights. As such, the adjunct 104 can have an uncompressed height which is greater than the fired height of the staples 106 disposed within the staple cartridge 102 (e.g., the height (H) of the fired staple 106a in FIG. 7). That is, the adjunct 104 can have an undeformed state in which a maximum height of the adjunct 104 is greater than a maximum height of a fired staple (e.g., a staple that is in a formed configuration). In such instances, the adjunct can be referred to as a "tissue thickness compensator." In one embodiment, the uncompressed height of the adjunct 104 can be about 10% taller, about 20% taller, about 30% taller, about 40% taller, about 50% taller, about 60% taller, about 70% taller, about 80% taller, about 90% taller, or about 100% taller than the fired height of the staples 106. In certain embodiments, the uncompressed height of the adjunct 104 can be over 100% taller than the fired height of the staples 106, for example.

The adjuncts can have a variety of configurations, and can be formed from various materials. In general, an adjunct can be formed from one or more of a film, a foam, an injection molded thermoplastic, a vacuum thermoformed material, a fibrous structure, an additive manufacturing material, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010, which is incorporated by reference herein in its entirety.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is incorporated by reference herein in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

In other embodiments, the adjunct can be formed using a 3D printing process(es) compatible with absorbable polymers. Non-limiting examples of suitable 3D printing processes include stereolithography (SLA or SL), material jetting, selective laser sintering (SLS), and fused filament fabrication as understood by a person skilled in the art.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are incorporated by reference herein in their entireties.

Materials

The adjuncts in accordance with the described techniques can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA) (e.g., Dexon and Neoveil), poly(lactic-co-glycolic acid) (PLGA), polycaprolactone (PCL), polyglycolide (PGL), trimethylene carbonate (TMC), polylactic acid (PLA) (e.g., Linvatec Bioscrew and Bionx Implants Smart Screw), poly(trimethylene carbonate (PTMC), polyethylene diglycolate (PEDG), poly(propylene fumarate) (PPF), polyethylene ether (PEE), poly(ethylene glycol) (PEG), poly(N-isopropylacrylamide, poly(amino acid), poly(epoxycarbonate), poly(2-oxypropylene carbonate), poly(diol citrates), polymethacrylate anhydrides, poly(ethoxyethylene diglycolate), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides (e.g., REVA ReZolve Stents), and tyrosine-based polyesteramides (e.g., TYRX). The copolymers can also include poly(lactic acid-co-polycaprolactone) (PLA/PCL) (e.g., 16-18 month hydrolyzed), poly (L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), LPLA/DLPLA (e.g., Optima), PLGA-PCL (e.g., 15:85 (PCL: 50% D,L-Lactide: 50% Glycolide), 40:60 (PCL: 50% D,L-Lactide: 50% Glycolide), and 40:60 (PCL: 85% D,L-Lactide: 15% Glycolide), PLGA-PCL-PLGA, and PLGA-PEG-PLGA.

An adjunct can also include special polymer terminations, including (meth)acrylate and organically-derived polymers. Non-limiting examples of organically-derived polymers include those derived from collagen (e.g., Avitene, Endoavitene, Instat, Integran, Veritas, and Microfibrillar Collagen (MFC)).

An adjunct can also include active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+ Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, NeoRecormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Non-limiting examples of anti-cancer agents include monoclonial antibodies, bevacizumab (Avastin), cellular/ chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), *vinca* alkaloids agents that inhibit mitosis and microtubule formation (e.g., Vinblastine, Vincristine, Vindesine, Vinorelbine), angiostatic inhibiting agents that inhibit cell growths or cell expansion (e.g., Axitinib (Inlyta), Bevacizumab (Avastin), Cabozantinib (Cometriq), Everolimus (Afinitor, Zortress) Lenalidomide (Revlimid), Pazopanib (Votrient), Ramucirumab (Cyramza), Regorafenib (Stivarga), Sorafenib (Nexavar), Sunitinib (Sutent), Thalidomide (Synovir, Thalomid), Vandetanib (Caprelsa), Zib-aflibercept (Zaltrap), antiangiogenic polysaccharide, aplidine (dehydrodidemnin B), sapogenins viz. 20(S)-protopanaxadiol, and 20(S)-protopanaxatriol), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

Exemplary medicants also include agents that encourage blood supply regeneration following coronary artery disease (CAD) (e.g., $VEGF_{165}$ protein, $AdVEGF_{165}$, $AdVEGF_{121}$, and $VEGF_{165}$ plasmid) or periphery artery disease (PAD) (e.g., $VEGF_{165}$ plasmid, $AdVEGF_{121}$, SB-509 (SFP-VEGF plasmid), $AdVEGF_{165}$, and Ad2-HIF1α-VP16 (WALK trial)).

Drug Release

An adjunct in accordance with the described techniques can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Exposure Condition Monitoring

Monitoring and/or tracking exposure of an adjunct and any medicant(s) retained therein to one or more exposure conditions can provide any number of benefits. Exposure conditions, also referred to as environmental condition, can affect performance of the adjunct, e.g., longevity, and/or can affect performance of the medicant(s) retained therein, e.g., viability, longevity, and potency. Viability of a medicant generally refers to efficacy of the medicant, e.g., the medicant's ability to produce a particular effect. Longevity of an adjunct generally refers to a length of time the adjunct can produce a particular effect, such as the adjunct's ability to degrade or dissolve in a patient's body and thereby release medicant(s) from the adjunct. Longevity of a medicant generally refers to a length of time the medicant can produce a particular effect. Potency of a medicant generally refers to an amount of the medicant needed to produce a particular effect. The monitoring or tracking of the adjunct and the medicant(s) retained therein from the point of packaging to administration, or a portion thereof, can allow for early identification of non-viable adjunct and non-viable medicants, as well as modification of a patient's treatment, e.g., providing additional medicant dosage to a patient to compensate for a medicant having experienced an exposure condition adversely affecting the medicant's performance, and/or shelf-life based upon the exposure monitoring or tracking. Thus, monitoring and/or tracking exposure of an adjunct and any medicant(s) retained therein may reduce the risk of implanting an adjunct that has been rendered ineffective due to exposure conditions, may reduce the risk of administering a medicant at a dosage that has been rendered ineffective due to exposure conditions, and may reduce the risk of a non-viable medicant being administered to a patient via implantation of the adjunct that retains the medicant therein.

In general, systems and methods described herein include active or passive sensing mechanisms, such as sensors, that can monitor at least one exposure condition of an adjunct and any medicant(s) retained therein. In some instances, the active or passive sensing mechanisms can also track the extent of the adjunct's and medicant(s)'s exposure, e.g., frequency, intensity, and/or duration. As a result, the information related to the exposure condition itself and/or the extent of exposure can be used to determine the effectiveness of the adjunct and any medicant(s) retained therein prior to implantation of the adjunct and/or prior to distribution in commerce of the adjunct that retains the medicant(s) therein.

Systems and methods described herein including an active or passive sensing mechanism can include a staple cartridge and an adjunct releasably coupled to the staple cartridge, such as any one or more of the staple cartridges and any one or more of the adjuncts discussed above. As also discussed above, the adjunct can retain one or more medicants therein, and the staple cartridge either can be fixedly coupled to a jaw of a surgical stapler or can be configured to be removably and replaceably coupled to a jaw of a surgical stapler. The medicants can include any one or more of the medicants discussed above.

In an exemplary embodiment, a packaging unit that packages the adjunct and the medicant(s) retained therein includes at least one active or passing sensing mechanism. At least one exposure condition of the adjunct and the medicant(s) retained therein can thus be monitored along the supply chain from when the adjunct and the medicant(s) retained therein are packaged by the packaging unit until removal of the adjunct and the medicant(s) retained therein from the packaging unit.

A packaging unit can package an adjunct with at least one medicant releasably retained therein with the adjunct being configured to be releasably coupled to a staple cartridge after the packaging unit is opened. Alternatively, a packaging unit can package an adjunct with at least one medicant releasably retained therein with the adjunct releasably coupled to a staple cartridge such that the packaging unit packages the adjunct, the at least one medicant, and the staple cartridge. In such embodiments, the staple cartridge having the adjunct releasably coupled thereto can be configured to be seated in an end effector of a surgical stapler after the packaging unit is opened, or the packaging unit can also package the surgical stapler with the staple cartridge seated in the stapler's end effector or with the staple cartridge being seatable in the stapler's end effector after the packaging unit is opened. In some embodiments, a packaging unit can package a plurality of adjuncts each having at least one medicant retained therein, and can optionally also package a plurality of staple cartridges each with one of the adjuncts releasably coupled thereto. Providing a plurality of adjuncts in a packaging unit may allow for different staples cartridges to be provided so a surgeon or other medical professional can choose an appropriately sized staple cartridge for use in a particular procedure, as staple cartridges are typically offered in different sizes for different surgical staplers and/or with differently sized staples and/or a different number of staples. Providing a plurality of adjuncts in a packaging unit may allow for a plurality of the same adjuncts to be provided to ease reloading of a surgical stapler during a surgical procedure with a series of the same adjuncts. Regardless of the elements packaged by a packaging unit, in an exemplary embodiment, the packaging unit is sterile to help ensure safe use of the packaged element(s) with a patient.

As mentioned above, a sensor can be configured to monitor or detect at least one exposure condition of an adjunct and any medicant(s) retained therein. Examples of exposure conditions include geographic location (e.g., as sensed by a location sensor configured to sense GPS or other location), time (e.g., as sensed by a timer or a clock device such as an atomic clock), date (e.g., as sensed by a timer), temperature (e.g., as sensed by a temperature sensor), ultraviolet (UV) exposure (e.g., as sensed by a UV sensor configured to sense UV level), pH (e.g., as sensed by a pH sensor configured to sense pH level), humidity (e.g., as sensed by a humidity sensor configured to sense humidity level), light (e.g., as sensed by a photo detector configured to sense light level), oxygen exposure (e.g., as sensed by an oxygen ($O_2$) sensor configured to sense oxygen level), vibration (e.g., as sensed by a vibration sensor, accelerometer, etc. configured to sense vibration), and atmospheric pressure (e.g., as sensed by a barometric pressure sensor configured to sense barometric pressure or an atmospheric pressure sensor configured to sense air pressure of ambient air). Alternatively, or in addition, the sensor can be configured to track the frequency, duration, and/or intensity of an adverse exposure event experienced by the adjunct and any medicant(s) retained therein prior to implantation of the adjunct, e.g., a spike of an exposure condition during transport or storage of the adjunct and any medicant(s) retained therein as sensed by a sensor configured to sense the exposure condition and a timer configured to provide date and time stamp data for the sensed data. One or more sensors can be used to monitor the at least one exposure condition. A sensor can configured to monitor a single exposure condition (e.g., monitor only time, monitor only geographic location, monitor only pH, monitor only light, etc.) or can be configured to sense at least two exposure conditions (e.g., monitor temperature and humidity, monitor time, date, and at least one other exposure condition, monitor light and UV light, etc.). U.S. Pat. Pub. No. 2002/0014951 entitled "Remote Control For A Hospital Bed" published Feb. 7, 2002 and U.S. Pat. Pub. No. 2007/0251835 entitled "Sub-network Synchronization And Variable Transmit Synchronization Techniques For A Wireless Medical Device Network" published Nov. 1, 2007 further discuss various exemplary sensors and are incorporated by reference herein in their entireties.

Temperature can adversely affect performance of an adjunct. For example, a temperature above a predetermined maximum threshold temperature or below a predetermined minimum threshold temperature can cause the adjunct to begin to degrade before implantation of the adjunct in a body of a patient and that, therefore, the adjunct should no longer be used. Temperature can also adversely affect performance of a medicant. For example, a temperature above a predetermined maximum threshold temperature or below a predetermined minimum threshold temperature, as appropriate for a particular medicant, can cause the medicant to lose potency and that, therefore, the adjunct having the medicant retained therein should no longer be used or, before the medicant is retained in the adjunct, that the medicant should not be retained in the adjunct.

UV exposure can adversely affect performance of an adjunct. For example, a UV level above a predetermined maximum threshold UV level or below a predetermined minimum threshold UV level, as appropriate for a particular adjunct's material(s), can cause the adjunct to begin to degrade before implantation of the adjunct in a body of a patient and that, therefore, the adjunct should no longer be used. UV level can also adversely affect performance of a medicant. For example, a UV level above a predetermined maximum threshold UV level or below a predetermined minimum threshold UV level, as appropriate for a particular medicant, can cause the medicant to lose potency and that, therefore, the adjunct having the medicant retained therein should no longer be used or, before the medicant is retained in the adjunct, that the medicant should not be retained in the adjunct.

Humidity can adversely affect performance of an adjunct. For example, a humidity above a predetermined maximum threshold humidity or below a predetermined minimum threshold humidity, as appropriate for a particular adjunct's material(s), can cause the adjunct to begin to degrade before implantation of the adjunct in a body of a patient and that, therefore, the adjunct should no longer be used. Humidity can also adversely affect performance of a medicant. For example, a humidity above a predetermined maximum threshold temperature or below a predetermined minimum threshold humidity, as appropriate for a particular medicant, can cause the medicant to lose potency and that, therefore, the adjunct having the medicant retained therein should no longer be used or, before the medicant is retained in the adjunct, that the medicant should not be retained in the adjunct.

Geographic location can be indicative of temperature and/or humidity exposure since temperature and humidity can be known for a particular location at a particular date and time. Geographic location can also be indicative of whether a medicant is approved for use in its current location, e.g., whether or not a medicant is exposed to an inappropriate geographic location and should thus not be used.

Light can adversely affect performance of a medicant. For example, a light level above a predetermined maximum threshold light level can cause the medicant to lose potency and that, therefore, the adjunct having the medicant retained therein should no longer be used or, before the medicant is retained in the adjunct, that the medicant should not be retained in the adjunct.

Oxygen can adversely affect performance of an adjunct. For example, exposure of the adjunct to an oxygen level above a predetermined maximum threshold oxygen level can cause the adjunct to lose sterility and/or begin to degrade before implantation of the adjunct in a body of a patient and that, therefore, the adjunct should no longer be used. If the adjunct is sealed in a sterile packaging unit, the oxygen exposure of the adjunct should not change until the packaging unit is opened for use. Thus, oxygen level being above a predetermined maximum threshold oxygen level at a particular date/time stamp can be indicative of sterility of the adjunct being lost such that the adjunct should no longer be used and/or that the adjunct may have started to degrade such that the adjunct should no longer be used.

Vibration can adversely affect performance of an adjunct. For example, exposure of an adjunct to vibration above a predetermined maximum vibration is indicative of the adjunct being impacted with force. The force may cause the adjunct to become compressed prematurely, e.g., before implantation, and thus not be able to properly compress and conform in a patient's body.

Atmospheric pressure can adversely affect performance of a medicant. For example, exposure of the medicant to an atmospheric pressure above a predetermined maximum threshold atmospheric pressure can cause the medicant to lose potency and that, therefore, the adjunct retaining the medicant therein should no longer be used.

Rushes or delays in the supply chain can have an impact on adjuncts and medicants. For example, production or storage delays of the adjunct and the medicant(s) retained therein can negatively affect the shelf-life of the adjunct or the medicant.

As mentioned above, a system can include one or more sensors. A sensor can be associated with at least one adjunct (and thus also with any medicants retained therein) and/or a packaging unit for the at least one adjunct (and thus also with any medicants retained therein). As discussed above, the one or more adjuncts in the packaging unit can be standalone elements or can be releasably coupled to a staple cartridge, which can be in the packaging unit as a standalone unit configured to be removably and replaceably seated in a jaw of an end effector of a surgical stapler or can be in the packaging unit already coupled to an end effector of a surgical stapler, such as by being fixedly seated in a jaw of the end effector or by being removably and replaceably seated in the jaw of the end effector.

The sensor can be used to monitor exposure conditions of the adjunct and any medicant(s) retained therein prior to the adjunct being implanted in a patient and thus before the medicant(s) are administered to a patient. This may help ensure that at the time of implantation the adjunct(s) can effectively release the medicant(s) and that at the time of medicant administration upon adjunct implantation and/or at time(s) thereafter, each of the one or more medicants is viable and is delivered at an effective dosage. Moreover, this monitoring may also aid in detection of non-viable adjuncts and/or non-viable medicants early on in the supply chain. As a result, manufacturers can recall non-viable adjuncts (and thus any medicant(s) retained therein) at an early stage, e.g., prior to packaging and/or distribution, which may lead to decreased recall costs and avoid the potential health risks to the patients.

The sensor can be configured to monitor at least one exposure condition of the adjunct and any medicants retained therein while the adjunct is seated in a staple cartridge (whether or not the staple cartridge is seated in a jaw of an end effector). Alternatively, or in addition, the sensor can be configured to monitor at least one exposure condition of the adjunct and any medicants retained therein while the adjunct and any medicants retained therein are within the packaging unit, e.g., whether or not the adjunct is packaged already attached to the staple cartridge. As such, the sensor can be configured to monitor at least one exposure condition of the medicant(s) after the medicant(s) are associated with the adjunct, e.g., after the medicant(s) have been retained by the adjunct but before the adjunct has been implanted in a patient. As a result, the sensor can function as a shelf-life monitor for the adjunct having the medicant(s) retained therein and as a shelf-life monitor for the medicant(s) once the medicant(s) are retained by the adjunct.

Data acquired by the sensor can be communicated to a processor through a communications interface. In an exemplary embodiment, the communications interface is associated with the adjunct or a staple cartridge seating the adjunct therein, and a packaging unit packaging the adjunct and the medicant(s) retained therein includes the communications interface, as discussed herein. The processor can be remote from or local to the adjunct and thus remote from or local to the packaging unit packaging the adjunct.

In use, once the data is received by the processor, the processor can process the data and provide a data output. In one example, the data output can be an expiration date of a medicant retained by an adjunct, which can be determined by taking into account the data acquired by the sensor. The processor can be configured to similarly process the data and provide a data output regarding the adjunct. For example, the processor can be configured to determine the expiration date by determining an elapsed amount of time after the medicant and adjunct have been packaged, as indicated by the sensor. The processor can also be configured to compare the determined elapsed amount of time with the medicant's and/or adjunct's predetermined expiration date as set by the manufacturer (or other quality controller) to determine whether the expiration date has passed. The processor can also be configured to adjust the elapsed amount of time based on the data acquired by the sensor to account for intensity and duration of any exposure condition of the packaged medicant and adjunct. The processor can be configured to access a lookup table that is stored in a memory and that store predetermined metrics for the medicant and/or the adjunct. The predetermined metrics can associate the medicant and/or the adjunct with each of one or more exposure conditions and indicate the exposure condition's effect on the medicant's and/or the adjunct's expiration date, e.g., by indicating how much time the medicant's and/or the adjunct's expiration date should be adjusted downward (if at all) for particular time durations of the exposure condition.

In some embodiments, the medicant's expiration date can be for a batch of the medicant. The processor can be configured to provide a data output indicating that the batch of the medicant, and thus that the medicant retained by the adjunct, is beyond its expiration date. For example, the data output can be in the form of a warning, such as a warning configured to be communicated via text and/or image display to a user such as by text message, email, display on a computer system's display screen, etc. The adjunct's expiration date can similarly be for a batch of adjuncts.

A warning as discussed herein can be to a user of the adjunct (and thus of the medicant retained by the adjunct) and/or to a third party, e.g., a manufacturer of the adjunct and/or the medicant, a cloud service configured to communicate with hospitals and/or other medical facilities that provide adjuncts to users, etc. Providing a warning to the user may help prevent the adjunct from being implanted, thereby helping prevent the adjunct and the medicant from being delivered to a patient, and thus help avoid adverse patient effects and/or allow the user to obtain a new adjunct for implantation. Providing a warning to the third party as a cloud service may (1) facilitate automatic product replacement by allowing the cloud service to automatically reorder the adjunct, staple cartridge coupled to the adjunct, and/or surgical stapler coupled to the staple cartridge that is coupled to the adjunct, (2) allow the cloud service to automatically generate a complaint report that is transmitted from the cloud service to another third party, e.g., a manufacturer of the adjunct and/or the medicant, a medical professional intended to implant the adjunct, etc., that the other third party may use to evaluate their business, take remedial action, etc., (3) allow the cloud service to automatically generate a request to a quality control unit, such as a quality control team at the adjunct's and/or medicant's manufacturer, for consultation of what step(s) the user, the user's health care provider (HCP), the adjunct's manufacturer, the medicant's manufacturer, and/or another party should take, and/or (4) associate the particular adjunct (e.g., as identified with a product identification code included in the warning) with a serialization that can be traced to a specific distribution leg in the supply chain, should the excursion happen with the user then the adjunct and/or the medicant retained therein may not be refundable or replaced due to a history of known user error and/or the user can be reminded of appropriate storage conditions for the adjunct, e.g., message shown on a display of a computer system, email sent to the user associated with the adjunct (and thus the medicant retained by the adjunct), a hospital or other medical care facility being informed of the user error(s) for discussion with the one or more parties responsible for proper storage and/or transport of the adjunct at the medical care facility, etc.

The warning can indicate that an adjunct (and thus any medicants retained by the adjunct) should not be used, e.g., because of adverse exposure condition(s) experienced by the adjunct (and any medicants retained by the adjunct). If an adjunct (and thus any medicants retained by the adjunct) is still usable but has experienced at least one adverse exposure condition, the warning can provide a recommendation of use that reflects the adverse exposure condition(s), such as a time period from the current time in which the adjunct should be implanted so the adjunct (and thus any medicants retained by the adjunct) maintain sufficient effectiveness. A warning may be provided even if an adjunct (and thus any medicants retained by the adjunct) has not experienced any exposure condition(s) that adversely affect its use in a surgical procedure, such as a time period from the current time in which the adjunct should be implanted so the adjunct (and thus any medicants retained by the adjunct) maintain sufficient effectiveness. For example, such a recommendation may be beneficial for an adjunct and/or a medicant that is adversely affected by light exposure. When a packaging unit that packages the adjunct and medicant(s) retained by the adjunct is opened, the adjunct and the medicant(s) are exposed to light, which may then start a time period in which the adjunct (and thus the medicant(s)) should be implanted before the adjunct and medicant(s) are exposed to too much light. For another example, such a recommendation may be beneficial for an adjunct and/or a medicant that is adversely affected by temperature and/or humidity exposure. An operating room can have a temperature sensor and/or a humidity sensor in communication with the processor providing the warning such that the warning can take into account the operating room's temperature and/or humidity to provide a time period from the current time in which the adjunct should be implanted so the adjunct (and thus any medicants retained by the adjunct) maintain sufficient effectiveness given its current exposure to conditions in the operating room.

Another example of the data output of the processor after the processor processes the data is an excursion condition state, which can be determined by taking into account the data acquired by the sensor. For example, the processor can be configured to compare data received from the sensor with a predetermined threshold or range indicative of a safe exposure condition. If the received data is outside of the predetermined safe range, above the predetermined safe threshold, or below the predetermined safe threshold as appropriate for the particular exposure condition, the data output can be in the form of a warning indicating that the packaging unit, and thus the adjunct(s) and any medicants retained by the adjunct(s), has experienced at least one exposure condition during its life so far in the supply chain that its performance has been adversely affected enough such that the packaged adjunct(s) retaining the medicant(s) therein should not be implanted.

Figure 8:
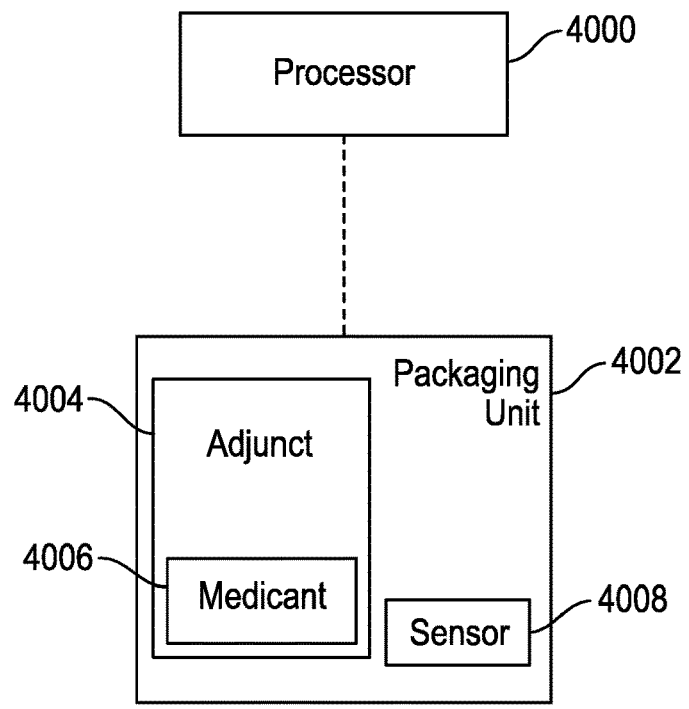
FIG. 8 is a schematic view of one exemplary embodiment of communication network including a processor and one exemplary embodiment of a packaging unit.

FIG. 8 shows an embodiment of a processor 4000 configured to communicate with a packaging unit 4002 packaging an adjunct 4004 retaining a medicant 4006 therein. The packaging unit 4002 in this illustrated embodiment is in the form of a blister pack, but other types of packaging units can be used. A sensor 4008 attached to the packaging unit 4002 is configured to monitor at least one exposure condition, as discussed herein, and incorporates a communications interface therein, e.g., an RFID sensor tag, a microcontroller including a sensor, power source, and a wireless transmitter, a flex circuit including a sensor, battery, and a wireless transmitter, etc., although a packaging unit can include a separate sensor and communications interface. The sensor 4008, e.g., the communications interface thereof, is configured to communicate data wirelessly with the processor 4000. The sensor 4008 can be attached to the packaging unit 4002 in any of a variety of ways, such as by being embedded in a material (e.g., a polymer, a reinforced cardboard, glass, etc.) forming the packaging unit 4002, being adhered to an inner surface or an outer surface of the packaging unit 4002 using adhesive, adhered to a label or sticker on the packaging unit 4002, or by being attached to the packaging unit 4002 using another attachment mechanism.

Figure 9:
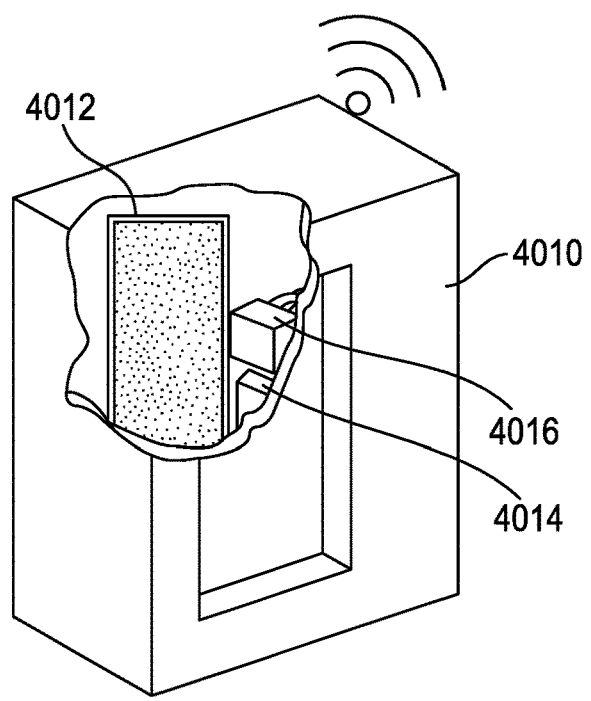
FIG. 9 is a partial-cutaway perspective view of another embodiment of a packaging unit.

FIG. 9 illustrates another embodiment of a packaging unit 4010 configured to communicate with a processor (not shown). The packaging unit 4010 in this illustrated embodiment is in the form of a box, but other types of packaging units can be used. The packaging unit 4010 in this illustrated embodiment packages an adjunct 4012 retaining a medicant (obscured in FIG. 9) therein. A sensor 4014 attached to the packaging unit 4010 is configured to monitor at least one exposure condition, as discussed herein. The packaging unit 4010 also includes an electrical contact 1016 that is configured to read the sensed data from the sensor 4012. The sensor 4014 and the electrical contact 1016 are contained in the packaging unit 4010 with the adjunct 4012. The sensor 1014 is positioned in close proximity to the electrical contact 1016. As such, once the sensor 1014 is positioned close to or in direct contact with the electrical contact 1016, the sensor 1014 is read by the electrical contact 1016 (e.g., a reader) and the data from the sensor 1014 can be transmitted via a communications interface of the packaging unit to a processor, as discussed herein. In this illustrated embodiment, the data is wirelessly transmitted to the processor using the packaging unit's communications interface, which is part of the electrical contact 1016 in this illustrated embodiment.

Figure 10:
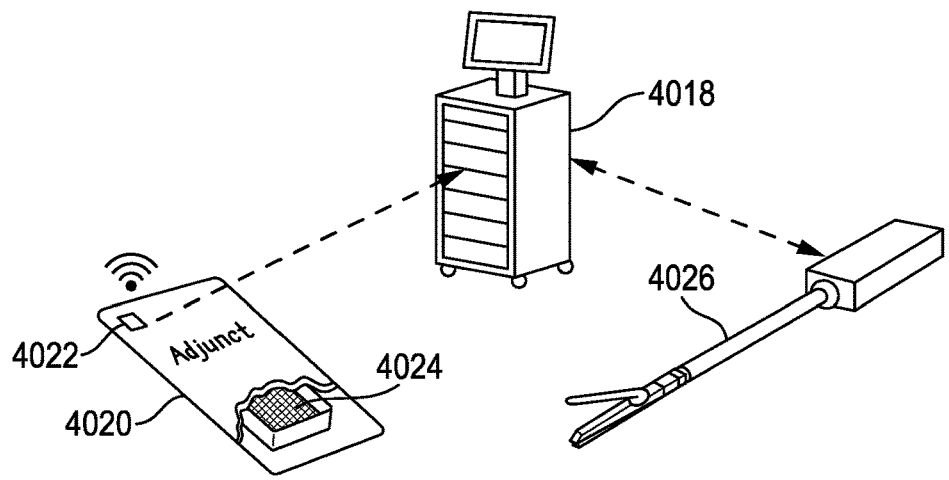
FIG. 10 is a perspective view of another embodiment of a communication network including another embodiment of a packaging unit, one exemplary embodiment of a surgical hub, and another embodiment of a surgical stapler.

A processor configured to communicate with a packaging unit can be a component of a computer system, such as an embodiment of a computer system 4018 shown in FIG. 10. The computer system 4018 is configured to communicate wirelessly with a packaging unit 4020, e.g., the packaging unit 4002 of FIG. 8, the packaging unit 4010 of FIG. 9, or other packaging unit, via a communications interface 4022, e.g., a QR code, an RFID tag, etc., of the packaging unit 4012. The communications interface 4022 can be part of a multi-functional component, such as a sensor including communications technology, a microcontroller including sensing and communicating technology, etc., or a separate sensor configured to communicate gathered data to the communications interface can be attached to the packaging unit 4020. The packaging unit 40202 in this illustrated embodiment packages an adjunct 4024 retaining a medicant (obscured in FIG. 10) therein. The computer system 4018 is also configured to communicate wirelessly with a surgical instrument 4026, e.g., via a communications interface (obscured in FIG. 10) of the surgical instrument 4026, which in this illustrated embodiment includes a linear surgical stapler but can be another type of surgical instrument as discussed herein. The computer system 4018 can have a variety of configurations, such as computer systems 4028, 4030 shown in FIG. 11 and FIG. 12, which are discussed further below.

The computer system 4018 in this illustrated embodiment includes a surgical hub. Surgical hubs are also discussed further below.

In some embodiments, a packaging unit can package a plurality of other packaging units, e.g., package a plurality of the packaging units 4010 of FIG. 9, package a plurality of the packaging units 4020 of FIG. 10, package a plurality of the packaging units 4010 of FIG. 9, and a plurality of the packaging units 4020 of FIG. 10, package a plurality of the packaging units 4002 of FIG. 8, or package a plurality of some other combination and/or type of packaging units. Such a packaging unit packaging a plurality of packaging units is generally referred to herein as a "bulk packaging unit." The bulk packaging unit can include a sensor and communications interface as described herein and thus serve as an exposure condition monitor for all of the packaging units packaged in the bulk packaging unit. Such a configuration may reduce overall cost since each of the packaging units packaged in the bulk packaging unit need not include a sensor and communications interface as described herein. However, for added reliability and/or to account for exposure after a packaging unit is removed from the bulk packaging unit, each of the packaging units packaged in the case can include a sensor and communications interface as described herein. The bulk packaging unit including the sensor and communications interface may help reduce concerns such as over-pressurization of a packaging unit's foil pouch that could break the pouch's sterile seal since the foil pouch will be in the bulk packaging unit when travelling long distances via air travel and thus have some protection from over-pressurization. A medicant may prematurely release if subjected to over-pressurization, so the bulk packaging unit may also help prevent premature medicant release.

Computer Systems

Figure 11:
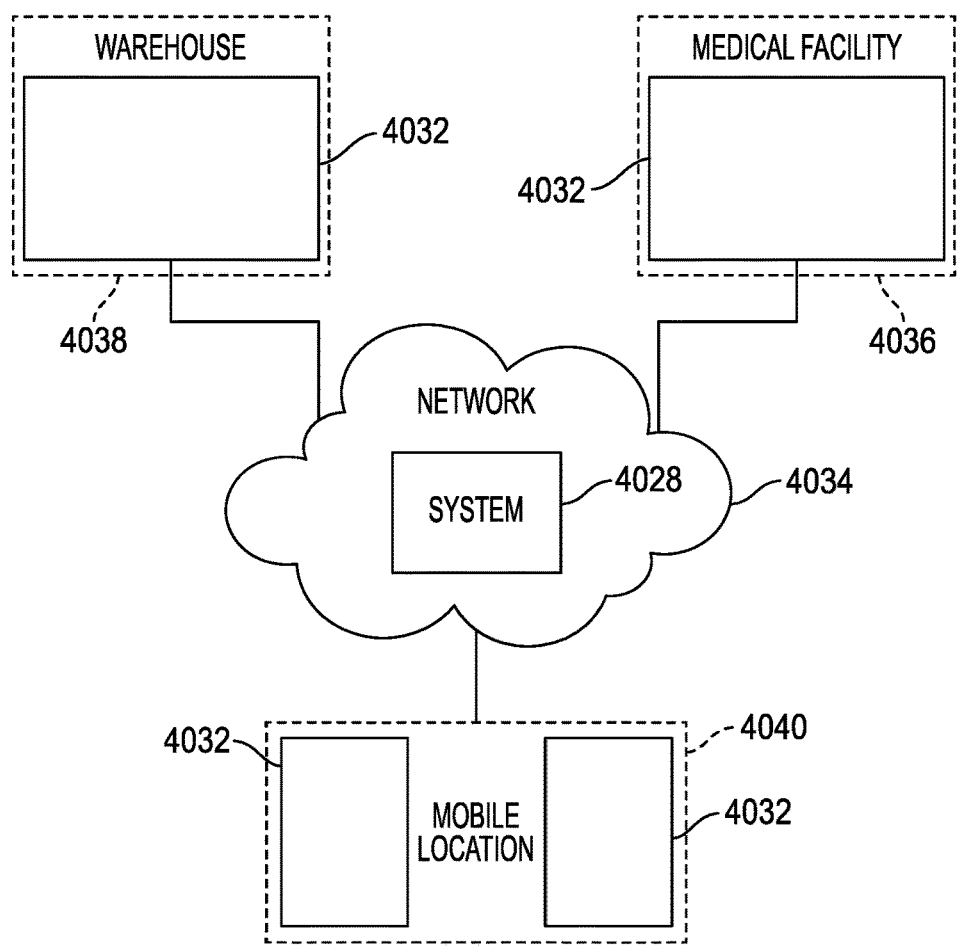
FIG. 11 is a schematic view of another embodiment of a communication network.

As mentioned above, a communications interface can be associated with an adjunct and/or a medicant retained by an adjunct, such as by a packaging unit that packages the adjunct and any medicants retained therein including the communications interface. Such a communications interface can be configured to communicate with a computer system, such a central computer system 4028 shown in FIG. 11. As shown in FIG. 11, a communications interface associated with a packaging unit 4032 packaging an adjunct having a medicant retained therein is configured to communicate with the central computer system 4028 through a communications network 4034 from any number of locations such as a medical facility 4036 (e.g., a hospital or other medical care facility), a warehouse 4038 (e.g., a distribution center or other stop in the packaging unit's supply chain), or a mobile location 4040 (e.g., between stops along the packaging unit's supply chain). The communications interface can be configured to access the computer system 4028 through a wired and/or wireless connection to the network 4034. In an exemplary embodiment, the communications interface is configured to access the computer system 4028 wirelessly, e.g., through Wi-Fi connection(s), which can facilitate accessibility of the computer system 4034 from almost any location in the world.

A person skilled in the art will appreciate that the computer system 4034 can include security features such that the aspects of the computer system 4034 available to any particular node can be determined based on, e.g., the identity of the node and/or the location from which the node is accessing the system. To that end, each node can have a unique key, username, password, and/or other security credentials to facilitate access to the computer system 4034.

The received security parameter information can be checked against a database of authorized nodes to determine whether the node is authorized and to what extent the node is permitted to interact with the computer system 4034, view information stored in the computer system 4034, and so forth.

As discussed herein, one or more aspects or features of the subject matter described herein, for example components of the central computer system 4034 and sensors, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communications network, e.g., the Internet, a wireless wide area network, a local area network, a wide area network, or a wired network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display screen, such as for example a cathode ray tube (CRT) or a liquid crystal display (LCD) or a light emitting diode (LED) monitor for displaying information to the user. The display screen can allow input thereto directly (e.g., as a touch screen) or indirectly (e.g., via an input device such as a keypad or voice recognition hardware and software). Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. As discussed herein, this feedback may be provided as a warning.

Figure 12:
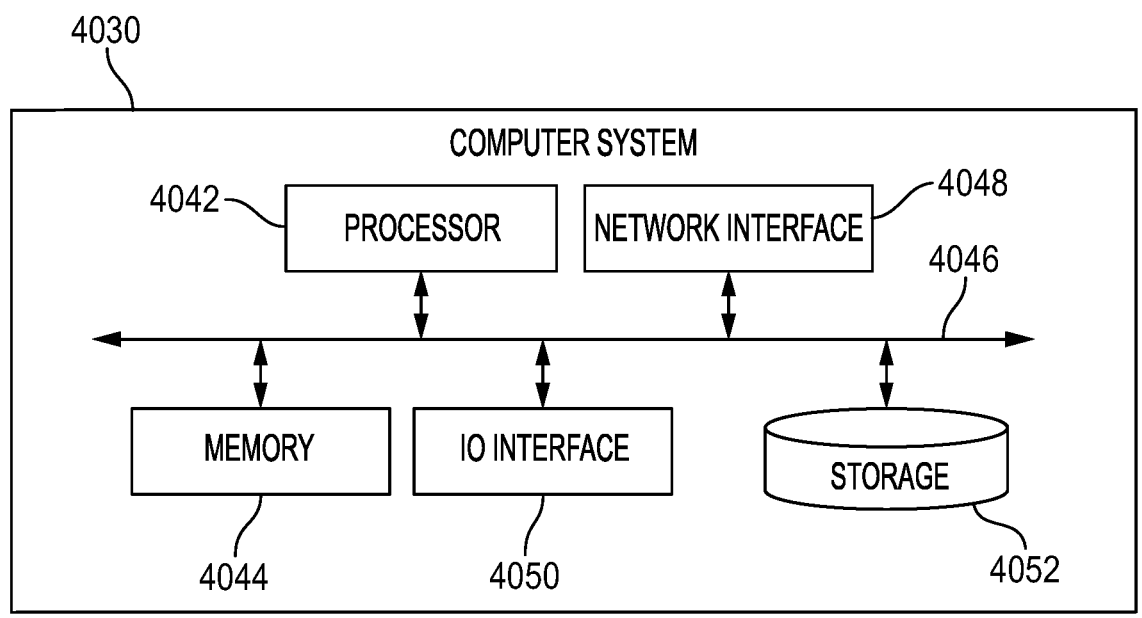
FIG. 12 is a schematic view of one exemplary embodiment of a computer system.

FIG. 12 illustrates one exemplary embodiment of the computer system 4028, depicted as computer system 4030. The computer system includes one or more processors 4042 configured to control the operation of the computer system 4030. The processor(s) 4042 can include any type of microprocessor or central processing unit (CPU), including programmable general-purpose or special-purpose microprocessors and/or any one of a variety of proprietary or commercially available single or multi-processor systems. The computer system 4030 also includes one or more memories 4044 configured to provide temporary storage for code to be executed by the processor(s) 4042 or for data acquired from one or more users, storage devices, and/or databases. The memory 4044 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system are coupled to a bus system 4046. The illustrated bus system 4046 is an abstraction that represents any one or more separate physical busses, communication lines/interfaces, and/or multi-drop or point-to-point connections, connected by appropriate bridges, adapters, and/or controllers. The computer system 4030 also includes one or more network interface(s) 4048 (also referred to herein as a communications interface), one or more input/output (TO) interface(s) 4050, and one or more storage device(s) 4052.

The communications interface(s) 4048 are configured to enable the computer system to communicate with remote devices, e.g., other communications interfaces or other computer systems, over a network, and can be, for example, remote desktop connection interfaces, Ethernet adapters, and/or other local area network (LAN) adapters. The IO interface(s) 4050 include one or more interface components to connect the computer system 4030 with other electronic equipment. For example, the IO interface(s) 4050 can include high speed data ports, such as universal serial bus (USB) ports, 1394 ports, Wi-Fi, Bluetooth, etc. Additionally, the computer system 4030 can be accessible to a human user, and thus the IO interface(s) 4050 can include displays, speakers, keyboards, pointing devices, and/or various other video, audio, or alphanumeric interfaces. The storage device(s) 4052, which may also be categorized as a memory, include any conventional medium for storing data in a non-volatile and/or non-transient manner. The storage device(s) 4052 are thus configured to hold data and/or instructions in a persistent state in which the value(s) are retained despite interruption of power to the computer system. The storage device(s) 4052 can include one or more hard disk drives, flash drives, USB drives, optical drives, various media cards, diskettes, compact discs, and/or any combination thereof and can be directly connected to the computer system or remotely connected thereto, such as over a network. In an exemplary embodiment, the storage device(s) 4052 include a tangible or non-transitory computer readable medium configured to store data, e.g., a hard disk drive, a flash drive, a USB drive, an optical drive, a media card, a diskette, or a compact disc.

The elements illustrated in FIG. 12 can be some or all of the elements of a single physical machine. In addition, not all of the illustrated elements need to be located on or in the same physical machine.

The computer system 4030 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 4030 can also include a web server for generating and/or delivering the web pages to client computer systems.

As shown in FIG. 11, the computer system 4030 of FIG. 12 as described above may form the components of the central computer system 4028 which is in communication with one or more communication interfaces each associated with at least one packaging unit. Data can be exchanged between the central computer system 4030 and the one or more communications interfaces. The computer system 4030 can also be configured to communicate with one or more additional computer systems.

In an exemplary embodiment, the computer system 4030 can be a single unit, e.g., a single server, a single desktop computer, a single laptop, a single mobile phone, a single electronic tablet, a single smart watch, a single tower, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system 4030 can also include any of a variety of other software and/or hardware components, including by way of example, operating systems and database management systems. Although an exemplary computer system is depicted and described herein, it will be appreciated that this is for sake of generality and convenience. In other embodiments, the computer system may differ in architecture and operation from that shown and described here. For example, the memory 4044 and storage device 4052 can be integrated together or a sensor can be included with the computer system 4030.

In an exemplary embodiment, a computer system to which data, e.g., data acquired by a sensor associated with an adjunct and/or regarding a medicant retained by an adjunct, includes a surgical hub. Exemplary embodiments of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068, 857 entitled "Adaptive Responses From Smart Packaging Of Drug Delivery Absorbable Adjuncts" filed Oct. 13, 2020, which are incorporated by reference herein in their entireties.

In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as surgical devices that are used to conduct medical procedures on patients, sensors configured to monitor exposure conditions, etc. The surgical hubs provide a wide array of functionality to improve the outcomes of medical procedures. The data generated by the various surgical devices, sensors, and surgical hubs about the patient and the medical procedure may be transmitted to the cloud-based medical analytics system. This data may then be aggregated with similar data gathered from many other surgical hubs, sensors, and surgical devices located at other medical facilities. Various patterns and correlations may be found through the cloud-based analytics system analyzing the collected data. Improvements in the techniques used to generate the data may be generated as a result, and these improvements may then be disseminated to the various surgical hubs and surgical devices. Due to the interconnectedness of all of the aforementioned components, improvements in medical procedures and practices may be found that otherwise may not be found if the many components were not so interconnected. Various examples of structures and functions of these various components are described in more detail in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068,857 entitled "Adaptive Responses From Smart Packaging Of Drug Delivery Absorbable Adjuncts" filed Oct. 13, 2020.

Figure 13:
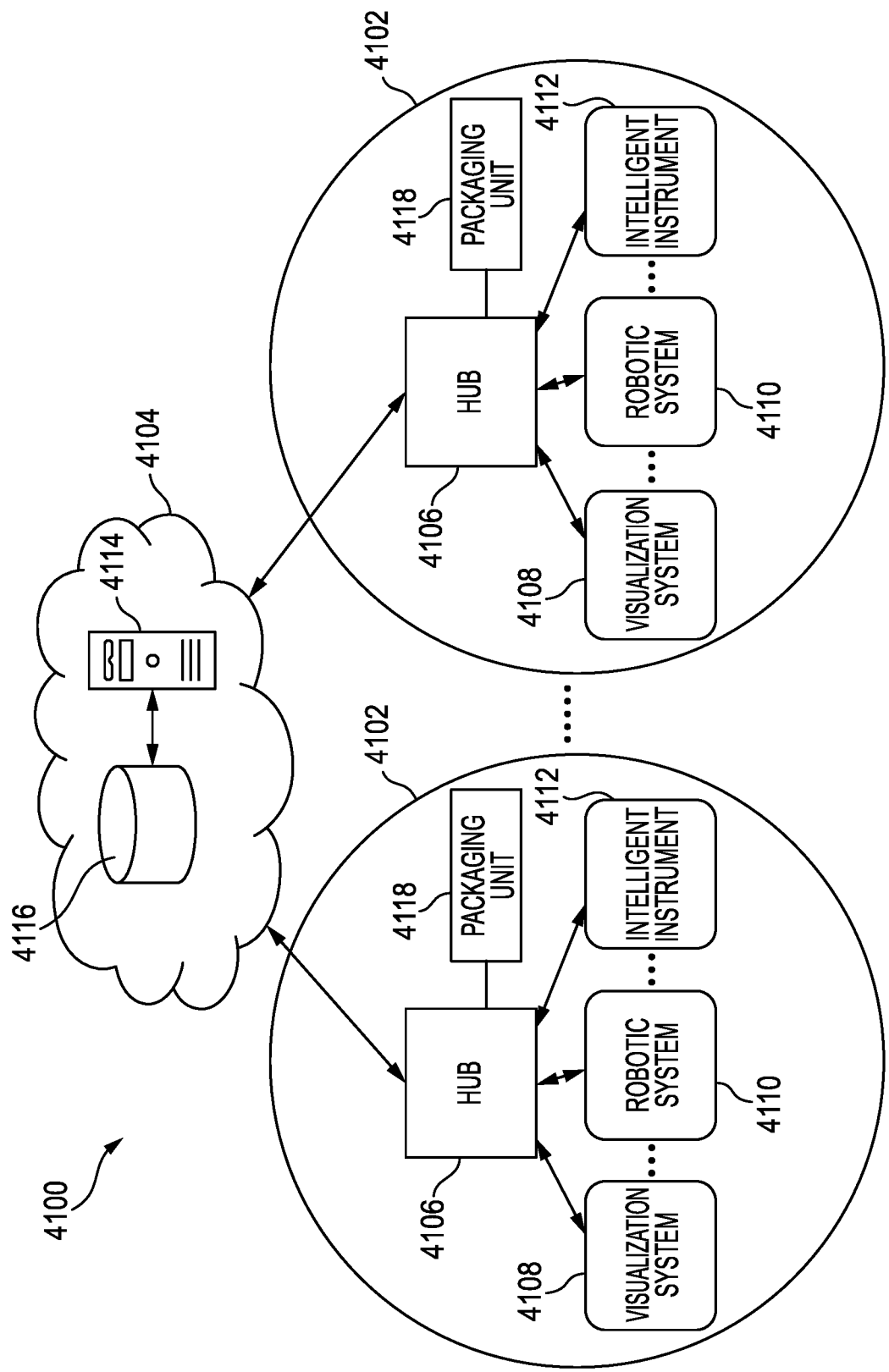
FIG. 13 is a schematic view of one exemplary embodiment of a computer-implemented interactive surgical system.

FIG. 13 illustrates an embodiment of a computer-implemented interactive surgical system 4100 that includes one or more surgical systems 4102 and a cloud-based system (e.g., a cloud 4104 that can include a remote computer system 4114 (a server in this illustrated embodiment) coupled to a storage device 4116). Each surgical system 4102 includes at least one surgical hub 4106 in communication with the cloud 4104. In one example, as illustrated in FIG. 13, the surgical system 4102 includes a visualization system 4108, a robotic system 4110, an intelligent surgical instrument 4112, and a packaging unit 4118 (e.g., packaging an adjunct having a medicant retained therein) which are configured to communicate with one another and/or the hub 4106. As discussed herein, in an exemplary embodiment, the packaging unit 4118 is configured to communicate with the surgical hub 4106, which can communicate with each of the visualization system 4108, the robotic system 4110, the intelligent surgical instrument 4112, and the packaging unit 4118. The surgical system 4102 can include an M number of hubs 4106, an N number of visualization systems 4108, an O number of robotic systems 4110, 4 a P number of 4 intelligent surgical instruments 4112, and a Q number of packaging units 4118, where M, N, O, P, and Q are integers greater than or equal to one that may or may not be equal to any one or more of each other. Various exemplary examples of suitable robotic systems, visualization systems, cloud-based analytics, and intelligent surgical instruments that can be used in a computer-implemented interactive surgical system are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068,857 entitled "Adaptive Responses From Smart Packaging Of Drug Delivery Absorbable Adjuncts" filed Oct. 13, 2020.

The surgical instruments 4112 in the system 4100 can be various types of tools. In an exemplary embodiment, the surgical instruments 4112 include surgical staplers configured to deliver an adjunct to tissue, such as the various surgical staplers and adjuncts discussed above. Thus, exposure conditions associated with adjuncts and medicant(s) retained therein can be communicated from the packaging units 4118 to their associated hubs 4106 and from the hubs 4106 to the cloud 4104, such as by communication interfaces of the packaging units 4118 each being configured to communicate sensed exposure condition data to the their associated one of the hubs 4106. The packaging units 4118 can also each be configured to communicate other data to the their associated one of the hubs 4106. The other data can include, for example, identification data that uniquely identifies the packaging unit 4118 and/or any one of more components packaged in and/or attached to the packaging unit 4118. Identification data can facilitate analysis of various useful metrics, such as surgical procedure outcomes, record of medicant delivery to the patient, record of adjunct delivery to the patient, etc. Data analysis may further employ outcome analytics processing, and using standardized approaches may provide beneficial feedback to either confirm surgical treatments and adjunct and/or medicant effectiveness or suggest modifications to surgical treatments, surgeon behavior, adjuncts, and/or medicants. For example, as discussed above, exposure conditions experienced by adjuncts and any medicant(s) retained therein can be monitored and tracked, which may facilitate analysis of how exposure conditions experienced by the adjunct and/or the medicant(s) retained by the adjunct affected surgical procedure outcomes, e.g., longer or shorter healing times, premature or delayed medicant release from the adjunct, etc., that can be used to modify a patient's post-operative treatment and/or to modify future evaluation of exposure conditions to help post-operatively observed adverse effects due to exposure conditions be accounted for in the future by, e.g., changing thresholds for exposure conditions.

Figure 14:
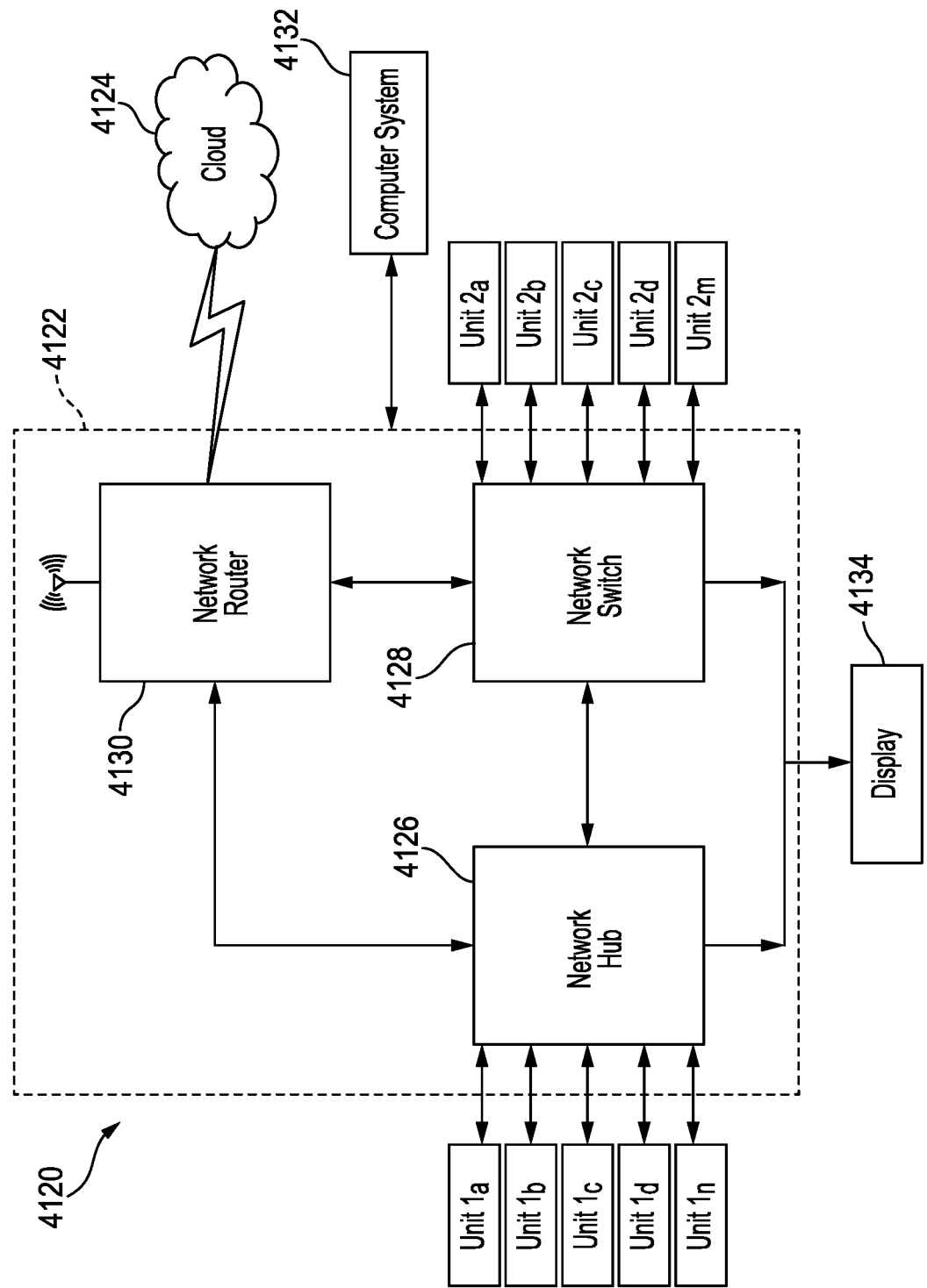
FIG. 14 is a schematic view of one exemplary embodiment of a surgical data network.

FIG. 14 illustrates one example of a surgical data network 4120 comprising a modular communication hub 4122, e.g., the hub 4106, configured to connect modular devices located in one or more operating theaters of a healthcare facility, or any room in a healthcare facility specially equipped for surgical operations, to a cloud-based system including a cloud 4124 that includes a remote server coupled to a storage device, e.g., the cloud 4104 that includes the remote server 4114 coupled to the storage device 4116. The modular communication hub 4122 includes a network hub 4126 and/or a network switch 4128 in communication with a network router 4130. The network hub 4126, the network switch 4128, and the network router 4130 define the communication hub's communications interface. The modular communication hub 4122 also can be coupled to a local computer system 4132 to provide local computer processing and data manipulation. The surgical data network 4120 can be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 4126 or network switch 4128. An "intelligent surgical data network" may be referred to as a "manageable hub" or "manageable switch." A switching hub reads the destination address of each packet and then forwards the packet to the correct port.

Modular units $1_a$-$1_n$, e.g., any number of packaging units such the packaging unit 4002 of FIG. 8, the packaging unit 4010 of FIG. 9, or other packaging unit, located in the operating theater can be coupled to the modular communication hub 4122. The network hub 4126 and/or the network switch 4128 can be coupled to the network router 4130 to connect the units $1_a$-$1_n$ to the cloud 4124 or the local computer system 4132. Data associated with the units $1_a$-$1_n$ can be transferred to cloud-based computers, e.g., to the cloud 4124, via the router 4130 for remote data processing and manipulation. Data associated with the units $1_a$-$1_n$ can also be transferred to the local computer system 4132 for local data processing and manipulation. Modular units $2_a$-$2_m$ located in the same operating theater also can be coupled to a network switch 4128. The network switch 4128 can be coupled to the network hub 4126 and/or the network router 4130 to connect to the units $2_a$-$2_m$ to the cloud 4124. Data associated with the units $2_a$-$2_n$ can be transferred to the cloud 4124 via the network router 4130 for data processing and manipulation. Data associated with the units $2_a$-$2_m$ can also be transferred to the local computer system 4132 for local data processing and manipulation. The numbers n, m of the units $1_a$-$1_n$/$2_a$-$2_m$ can be the same as or different from one another.

A person skilled in the art will appreciate that the surgical data network 4120 can be expanded by interconnecting multiple network hubs 4126 and/or multiple network switches 4128 with multiple network routers 4130. The modular communication hub 4122 can be contained in a modular control tower configured to receive multiple units $1_a$-$1_n$/$2_a$-$2_m$. The local computer system 4132 also can be contained in a modular control tower. The modular communication hub 4122 is connected to a display 4134 configured to display data obtained by at least some of the units $1_a$-$1_n$/$2_a$-$2_m$, and/or such data (and/or other data) analyzed by the cloud 4124 and/or the local computer system 4132, for example during surgical procedures.

The surgical data network 4120 can include a combination of network hub(s), network switch(es), and network router(s) connecting the units $1_a$-$1_n$/$2_a$-$2_m$ to the cloud 4124. Any one of or all of the units $1_a$-$1_n$/$2_a$-$2_m$ coupled to the network hub 4126 or network switch 4128 can collect data in real time and transfer the data to cloud computers for data processing and manipulation. Alternatively or in addition, any one or all of the units $1_a$-$1_n$/$2_a$-$2_m$ coupled to the network hub 4126 or network switch 4128 can transfer previously collected data, such as exposure condition data, to cloud computers for data processing and manipulation, e.g., once the one or all of the units $1_a\text{-}1_n/2_a\text{-}2_m$ is operatively connected to the cloud 4126 via the communication hub 4122. A person skilled in the art will appreciate that cloud computing relies on sharing computing resources rather than having local servers or personal devices to handle software applications. The term "cloud" can be used as a metaphor for "the Internet," although the term is not limited as such. Accordingly, the term "cloud computing" may be used herein to refer to "a type of Internet-based computing," where different services, such as servers, storage, and applications, are delivered to the modular communication hub 4122 and/or the computer system 4132 located in the surgical theater (e.g., a fixed, mobile, temporary, or field operating room or space) and to devices connected to the modular communication hub 4122 and/or the computer system 4132 through the Internet. The cloud infrastructure can be maintained by a cloud service provider. In this context, the cloud service provider can be the entity that coordinates the usage and control of the units $1_a\text{-}1_n/2_a\text{-}2_m$ located in one or more operating theaters. The cloud computing services can perform a large number of calculations based on the data gathered by packaging units, robots, and other computerized devices located in the operating theater. The hub hardware enables multiple devices or connections to be connected to a computer that communicates with the cloud computing resources and storage. Applying cloud computer data processing techniques on the data collected by the units $1_a\text{-}1_n/2_a\text{-}2_m$, the surgical data network may provide improved surgical outcomes, reduced costs, and/or improved patient satisfaction.

The operating theater devices $1_a\text{-}1_n$ can be connected to the modular communication hub 4122 over a wired channel or a wireless channel depending on the configuration of the units $1_a\text{-}1_n$ to a network hub, although as mentioned above wireless communication is used with packaging units in an exemplary embodiment. The network hub 4126 can be implemented as a local network broadcast device that works on the physical layer of the Open System Interconnection (OSI) model. The network hub 4126 provides connectivity to the units $1_a\text{-}1_n$ located in the same operating theater network. The network hub 4126 collects data in the form of packets and sends them to the router 4130 in half duplex mode. The network hub 4126 does not store any media access control/Internet Protocol (MAC/IP) to transfer the device data. Only one of the unit $1_a\text{-}1_n$ can send data at a time through the network hub 4126. The network hub 4126 has no routing tables or intelligence regarding where to send information and broadcasts all network data across each connection and to a remote server over the cloud 4124. The network hub 4126 can detect basic network errors such as collisions, but having all information broadcast to multiple ports can be a security risk and cause bottlenecks.

The units $2_a\text{-}2_m$ can be connected to the network switch 4128 over a wired channel or a wireless channel, although as mentioned above wireless communication is used with packaging units in an exemplary embodiment. The network switch 4128 works in the data link layer of the OSI model. The network switch 4128 is a multicast device for connecting the units $2_a\text{-}2_m$ located in the same operating theater to the network. The network switch 4128 sends data in the form of frames to the network router 4130 and works in full duplex mode. Multiple units $2_a\text{-}2_m$ can send data at the same time through the network switch 4128. The network switch 4128 can store and use MAC addresses of the units $2_a\text{-}2_m$ to transfer data.

The network hub 4126 and/or the network switch 4128 are coupled to the network router 4130 for connection to the cloud 4124. The network router 4130 works in the network layer of the OSI model. The network router 4130 creates a route for transmitting data packets received from the network hub 4126 and/or the network switch 4128 to cloud-based computer resources for further processing and manipulation of the data collected by any one of or all the units $1_a\text{-}1_n/2_a\text{-}2_m$. The network router 4130 can be employed to connect two or more different networks located in different locations, such as, for example, different operating theaters of the same healthcare facility or different networks located in different operating theaters of different healthcare facilities. The network router 4130 sends data in the form of packets to the cloud 4124 and works in full duplex mode. Multiple units can send data at the same time. The network router 4130 uses IP addresses to transfer data.

In one example, the network hub 4126 can be implemented as a USB hub, which allows multiple USB devices to be connected to a host computer. The USB hub can expand a single USB port into several tiers so that there are more ports available to connect units to the host system computer. The network hub 4126 can include wired or wireless capabilities to receive information over a wired channel or a wireless channel. A wireless USB short-range, high-bandwidth wireless radio communication protocol can be employed for communication between the units $1_a\text{-}1_n$ and units $2_a\text{-}2_m$ located in the operating theater.

In other examples, the units $1_a\text{-}1_n/2_a\text{-}2_m$ can communicate to the modular communication hub 4122 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the units $1_a\text{-}1_n/2_a\text{-}2_m$ can communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module can include a plurality of communication modules. For example, a first communication module may be dedicated to shorter-range wireless communications such as Wi-Fi and Bluetooth, and a second communication module can be dedicated to longer-range wireless communications such as GPS, EDGE, GPRS, CDMA, WiMAX, LTE, Ev-DO, and others.

The modular communication hub 4122 can serve as a central connection for one or all of the operating theater units $1_a\text{-}1_n/2_a\text{-}2_m$ and handle a data type known as frames. Frames carry the data generated by the units $1_a\text{-}1_n/2_a\text{-}2_m$. When a frame is received by the modular communication hub 4122, it is amplified and transmitted to the network router 4130, which transfers the data to the cloud computing resources by using a number of wireless or wired communication standards or protocols, as described herein.

The modular communication hub 4122 can be used as a standalone device or be connected to compatible network hubs and network switches to form a larger network. The modular communication hub 4122 is generally easy to install, configure, and maintain, making it a good option for networking the units $1_a\text{-}1_n/2_a\text{-}2_m$.

Figure 15:
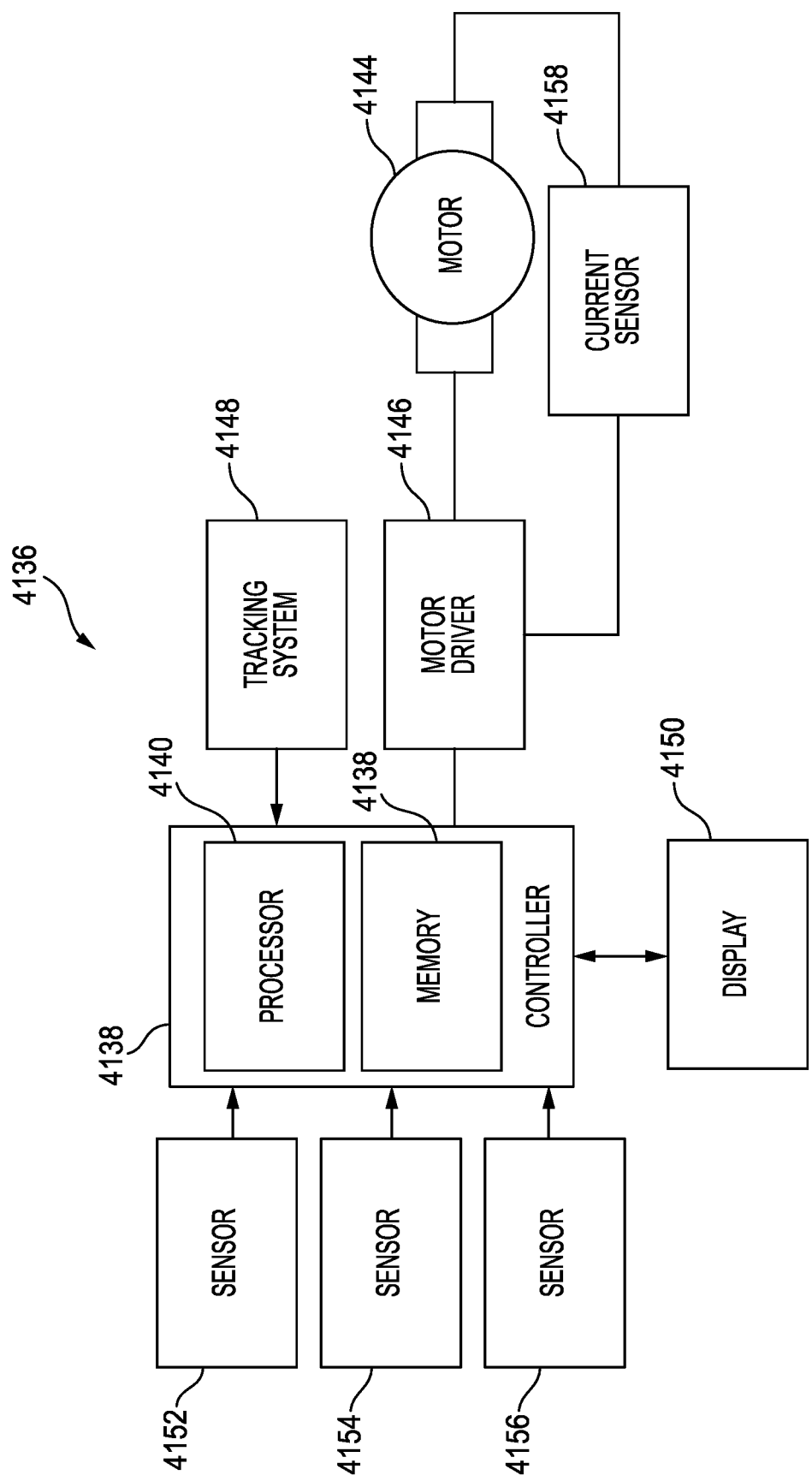
FIG. 15 is a logic diagram of one exemplary embodiment of a control system of a surgical instrument.

FIG. 15 illustrates an embodiment of a control system 4136 of a surgical instrument or tool, e.g., a surgical stapler as described herein. The control system 4136 includes a control circuit. The control circuit includes a controller that in this illustrated embodiment includes a microcontroller 4138 including a processor 4140 and a memory 4142. The microcontroller 4138 can be any single-core or multicore processor such as those known under the trade name ARM Cortex by Texas Instruments. A motor 4144, driven by a motor driver 4146, operably couples a longitudinally movable displacement member, such as a closure tube, a firing bar, an E-beam, and/or a knife, to fire staples, close jaws, and/or cut tissue, as discussed above. A tracking system 4148 is configured to determine the position of the longitudinally movable displacement member. The position information is provided to the processor 4140, which can be programmed or configured to determine the position of the longitudinally movable displacement member. Additional motors can be provided at the tool driver interface to control firing, closure tube travel, shaft rotation, and articulation. A display 4150 displays a variety of operating conditions of the instrument and can include touch screen functionality for data input. Information displayed on the display 4150 can be overlaid with images acquired via endoscopic imaging modules.

The microcontroller 4138 can be programmed to perform various functions such as precise control over the speed and position of knife and end effector articulation systems. The microcontroller 4138 can be configured to compute a response in the software of the microcontroller 4138. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor 4144 can be a brushed direct current (DC) motor with a gearbox and mechanical links to an articulation or knife system. The motor driver 4146 can be an A3941 available from Allegro Microsystems, Inc. Other motor drivers can be readily substituted for use in the tracking system 4148 including an absolute positioning system. Further description of absolute positioning systems is provided in U.S. Pat. Pub. No. 2017/0296213 entitled "Systems And Methods For Controlling A Surgical Stapling And Cutting Instrument" published Oct. 19, 2017, which is incorporated by reference herein in its entirety.

The motor 4144 can be controlled by the motor driver 4146 and can be employed by the firing system of the surgical instrument or tool. In various forms, the motor 4144 can be a brushed DC driving motor having a maximum rotational speed of approximately 25,000 RPM. In other arrangements, the motor 4144 can include a brushless motor, a cordless motor, a synchronous motor, a stepper motor, or any other suitable electric motor. The motor driver 4146 can include an H-bridge driver comprising field-effect transistors (FETs), for example. The motor 4144 can be powered by a power assembly releasably mounted to the handle assembly or tool housing for supplying control power to the surgical instrument. The power assembly can include a battery, which can include a number of battery cells connected in series that can be used as the power source to power the surgical instrument. In certain circumstances, the battery cells of the power assembly can be replaceable and/or rechargeable. For example, the battery cells can be lithium-ion batteries which can be couplable to and separable from the power assembly. The motor driver 4146 can be, for example, an A3941 available from Allegro Microsystems, Inc.

One or more of the control system's sensors 4152, 4154, 4156, 4158 can be configured to provide real-time feedback to the processor 4140. At least one of the sensors 4152, 4154, 4156, 4158 can be configured to monitor at least one operational parameter related to operation of the surgical instrument during a surgical procedure.

One example of a sensor configured to monitor an operational parameter includes a positon sensor configured to provide a unique position signal corresponding to the location of a displacement member, such as by being configured to measure linear displacement. Linear displacement sensors can include contact or non-contact displacement sensors. Examples of linear displacement sensors include linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, and any combination thereof.

Another example of a sensor configured to monitor an operational parameter is a strain gauge or a micro-strain gauge configured to measure one or more parameters of the surgical instrument's end effector. The measured strain is converted to a digital signal and provided to the processor 4140. For example, the strain gauge or micro-strain gauge can be configured to measure an amplitude of strain exerted on the surgical instrument's anvil during a clamping operation, which can be indicative of closure forces applied to the anvil and indicative of tissue compression. For example, the strain gauge or micro-strain gauge can be configured to measure a force applied to tissue by the surgical instrument's end effector.

Another example of a sensor configured to monitor an operational parameter is a load sensor configured to measure the closure force applied by the surgical instrument's closure drive system to the anvil. The load sensor can be configured to measure a firing force applied to an E-beam (or an I-beam) in a firing stroke of the surgical instrument.

Another example of a sensor configured to monitor an operational parameter is a load sensor configured to measure a force used to operate the cutting element, e.g., knife, of the surgical instrument that cuts tissue captured between the end effector's jaws.

Another example of a sensor configured to monitor an operational parameter is a magnetic field sensor configured to measure thickness of tissue captured between the end effector's jaws. The measurement of the magnetic field sensor can be converted to a digital signal and provided to the processor 4140.

Another example of a sensor configured to monitor an operational parameter is a current sensor 4158 configured to measure current drawn by the motor 4144. A force required to advance the firing member can correspond to the current drawn by the motor 4144, for example. The measured force is converted to a digital signal and provided to the processor 4140.

Measurements of tissue compression, tissue thickness, and/or force required to close the end effector on tissue can be used by the microcontroller 4138 to characterize the selected position of the firing member, the corresponding value of the speed of the firing member, and/or motor power level. For example, the memory 4142 can store a technique, an equation, and/or a lookup table which can be employed by the microcontroller 4138 in the assessment.

Sensors configured to sense operational parameters and uses of sensor-measured data, including to control operation of the surgical instrument using a robotic surgical system, are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0201140 entitled "Surgical Hub Situational Awareness" filed Mar. 29, 2018, and U.S. patent application Ser. No. 17/068,857 entitled "Adaptive Responses From Smart Packaging Of Drug Delivery Absorbable Adjuncts" filed Oct. 13, 2020.

The control system 4136 of the surgical instrument can include a wired or wireless communications interface configured to communicate with a modular communication hub, such as the modular communication hub 4122 of FIG. 14.

Analysis of Exposure Conditions

As discussed above, one or more exposure conditions of an adjunct and any medicant(s) therein can be monitored, such as by using one or more sensors of a packaging unit, and a processor, such as of a surgical hub or other computer system, can be configured to receive data gathered by the one or more sensors regarding the one or more exposure conditions. As also discussed above, the processor can be in operative communication with a memory configured to store data therein. The stored data can include predetermined threshold(s) for each of one or more exposure conditions that the processor may receive data regarding from a data module. Each of the predetermined threshold(s) can be associated with a particular medicant (or family of related medicants) and/or a particular adjunct (or family of related adjuncts, such as adjuncts all made from a same material). The processor can be configured to compare received exposure condition data to the predetermined threshold for the corresponding exposure condition and element (medicant and/or adjunct), and provide data output.

Figure 16:
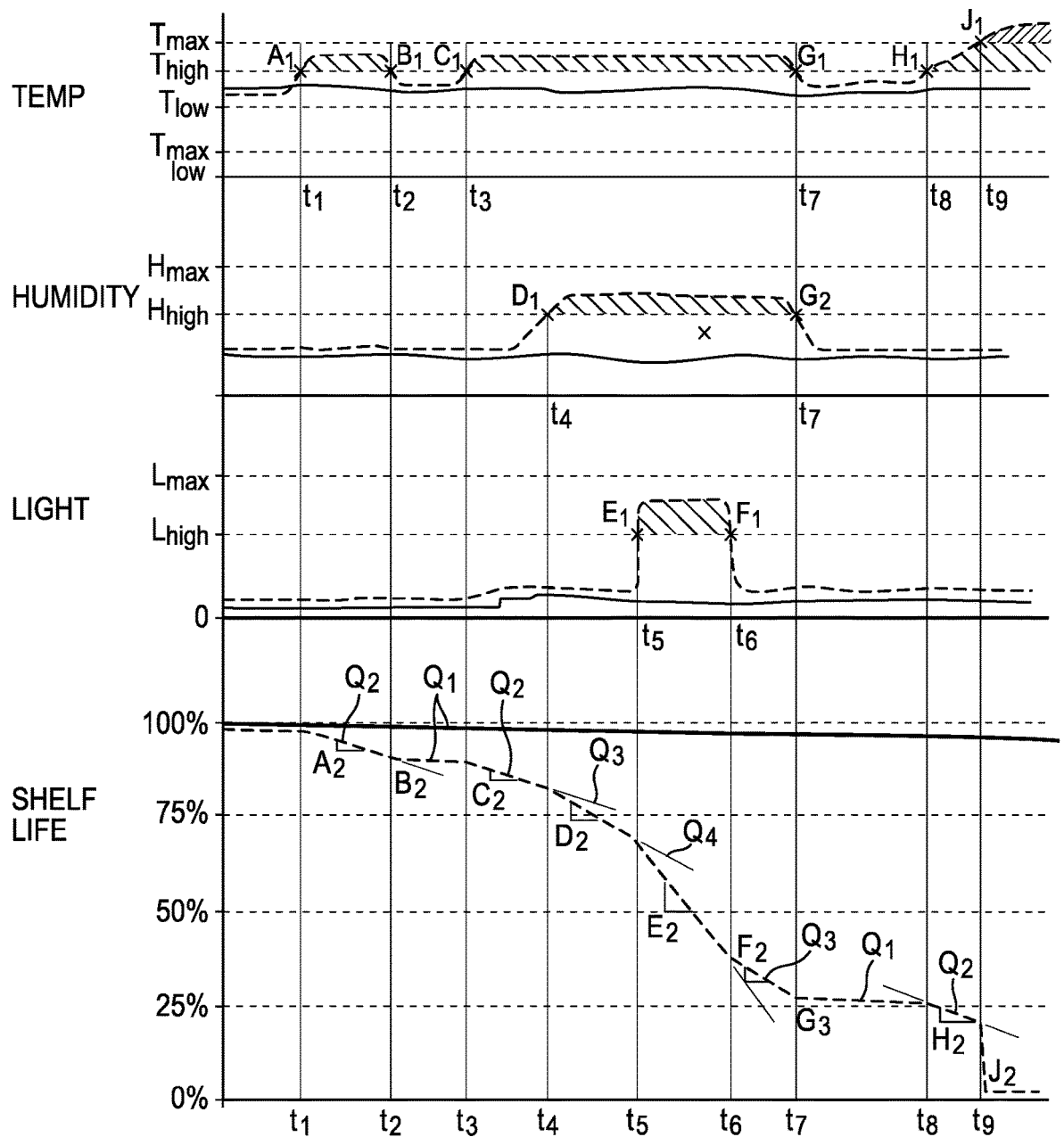
FIG. 16 is a graph showing exposure conditions and shelf life over time.

One embodiment of exposure condition data and processor analysis is shown in FIG. 16. In this illustrated embodiment, the processor is configured to determine a rate of shelf life degradation of an adjunct packaged by a packaging unit based on measurements of temperature, humidity, and light. As discussed above, the adjunct has at least one medicant retained therein, and the packaging unit can package other components therein such as at least one cartridge body, one or more additional adjuncts, etc. As shown in FIG. 16, a sensor of the packaging unit, e.g., the sensor 4008 of FIG. 8, the sensor 4014 of FIG. 9, the sensor 4022 of FIG. 10, etc., can be configured to track temperature, humidity, and light exposure over nine different time intervals $t_1$, $t_2$, $t_3$, $t_4$, $t_5$, $t_6$, $t_7$, $t_8$, $t_9$. As mentioned above, the sensor can be a single sensor configured to monitor multiple exposure conditions or can be a plurality of sensors each configured to sense at least one of the exposure conditions. The following discussion is also applicable to other exposure conditions, e.g., ultraviolet, pressure, etc.

A memory operably coupled to the processor has predetermined thresholds stored therein for each of temperature, light, and humidity. For temperature, the predetermined thresholds include a low temperature maximum $T_{MaxLow}$, a low temperature $T_{Low}$, a high temperature $T_{High}$, and a high temperature maximum $T_{Max}$. A temperature range between the low temperature $T_{Low}$ and the high temperature $T_{High}$ is an acceptable temperature range for the adjunct in which the temperature will not adversely affect shelf life. A temperature below the low temperature $T_{Low}$, and/or below the temperature maximum $T_{MaxLow}$ will adversely affect shelf life. A temperature below the temperature maximum $T_{MaxLow}$ indicates that the adjunct has been exposed to an adverse enough temperature that the adjunct not be used. A temperature above the high temperature $T_{High}$ and/or above the high temperature maximum $T_{Max}$ will adversely affect shelf life. A temperature above the high temperature maximum $T_{Max}$ indicates that the adjunct has been exposed to an adverse enough temperature that the adjunct not be used. As shown in FIG. 16, from time zero to time $t_1$, between time $t_2$ and time $t_3$, and between time $t_7$ and time $t_8$ the temperature is sensed to be in the acceptable range; between time $t_1$ and time $t_2$, between time $t_3$ and time $t_7$, and between time $t_8$ and $t_9$ the temperature is sensed to be above the high temperature $T_{High}$ and below the high temperature maximum $T_{Max}$, and after time $t_9$ the temperature is sensed to be above the high temperature maximum $T_{Max}$.

For humidity, the predetermined thresholds include a high humidity $H_{High}$ and a humidity maximum $H_{Max}$. A humidity above the high humidity $H_{High}$ and/or above the humidity maximum $H_{Max}$ will adversely affect shelf life. A humidity above the humidity maximum $H_{Max}$ indicates that the adjunct has been exposed to an adverse enough humidity that the adjunct not be used. As shown in FIG. 16, from time zero to time $t_4$ and from time $t_7$ forward the humidity is sensed to be in the acceptable range below the high humidity $H_{High}$, and from time $t_4$ to time $t_7$ the humidity is sensed to be above the above the high humidity $H_{High}$ and below the humidity maximum $H_{Max}$.

For light, the predetermined thresholds include a high light $L_{High}$ and a light maximum $L_{Max}$. Zero light indicates darkness (no light exposure). A light above the high light $L_{High}$ and/or above the light maximum $L_{Max}$ will adversely affect shelf life. A light above the light maximum $L_{Max}$ indicates that the adjunct has been exposed to an adverse enough light that the adjunct not be used. As shown in FIG. 16, from time zero to time $t_5$ and from time $t_6$ forward the light is sensed to be in the acceptable range below the high light $L_{High}$, and from time $t_5$ to time $t_6$ the light is sensed to be above the high light $L_{High}$ and below the light maximum $L_{Max}$.

In general, the shelf life of the adjunct is affected adversely at a first rate when only one of the exposure conditions is outside the acceptable range at the same time, is affected at a second rate greater than the first rate when two of the three of the exposure conditions are outside the acceptable range at the same time, and is affected at a third rate greater than the second rate when all three of the exposure conditions are outside the acceptable range at the same time. For example, as shown in FIG. 16, the shelf life of the adjunct decreases at a first, very low rate $Q_1$ when all of temperature, humidity, and light are sensed to be in their respective acceptable ranges from time zero to time $t_1$, from time $t_2$ to time $t_3$, and time $t_7$ to time $t_8$. The passage of time accounts for the first rate $Q_1$ of shelf life reduction. When only temperature is sensed to be outside the acceptable temperature range from time $t_1$ to time $t_2$, from time $t_3$ to time $t_4$, and from time $t_8$ forward, the shelf life of the adjunct reduces at a second rate $Q_2$ that is greater than the first rate $Q_1$. When each of temperature and humidity are sensed to be outside their respective acceptable ranges and light is sensed to be within its acceptable range from time $t_4$ to time $t_5$, the shelf life of the adjunct reduces at a third rate $Q_3$ that is greater than the second rate $Q_2$. The third rate $Q_3$ is about three times greater than the first rate $Q_1$ in this illustrated embodiment where the adverse exposure conditions are temperature and humidity. When all of temperature, humidity, and light are sensed to be outside their respective acceptable ranges from time $t_5$ to time $t_6$, the shelf life of the adjunct reduces at a fourth rate $Q_4$ that is greater than the third rate $Q_3$. The fourth rate $Q_4$ is about five times greater than the first rate $Q_1$ in this illustrated embodiment where the adverse exposure conditions are temperature, light, and humidity.

When the shelf life reaches 0%, the processor determines that the adjunct is no longer fit for use. If before the shelf life reaches 0% the adjunct experiences a fatal exposure event, the processor determines that the adjunct is no longer fit for use. In this illustrated embodiment, the adjunct experiences a fatal exposure event before the shelf life reaches 0% by the temperature being sensed to be above the high temperature maximum $T_{Max}$ at time $t_9$. The processor thus determines that the adjunct is no longer fit for use after $t_9$. In some embodiments, instead of waiting until the shelf life reaches 0% to determine that the adjunct is no longer fit for use, the percentage threshold for such an unfit determination can be a percentage above zero, such as 15%, 10%, 5%, 8%, 3%, 2%, etc. The unfit threshold percentage being above 0% reflects that even though the adjunct has some remaining shelf life, the life is low enough that an adjunct with greater shelf life should be used to help ensure adjunct effectiveness in a patient.

If the processor determines that the adjunct is unfit for use, e.g., has a shelf life of 0% (or other predetermined threshold for non-viability) or any one or more of the exposure conditions has been sensed to be at a fatal level (temperature above the high temperature maximum $T_{Max}$, humidity above the humidity maximum $H_{Max}$, light above the light maximum $L_{Max}$, the processor is configured to transmit a data output characterizing the determination so that a warning to not use the adjunct can be provided as discussed herein (e.g., email warning, visual warning on a display, audible warning, tactile warning, etc.) and/or to transmit a data output causing such a warning to be provided. The processor can be similarly configured to transmit a data output to indicate an adjunct's current determined shelf life, which may help a surgeon or other medical professional decide whether or not to use the adjunct. The processor can be similarly configured to transmit a data output to indicate any times when the adjunct experiences an adverse exposure event and indications of the exposure event, which may help a manufacturer, distributor, or other provider evaluate storage conditions and/or transport options for its packaging unit.

Figure 17:
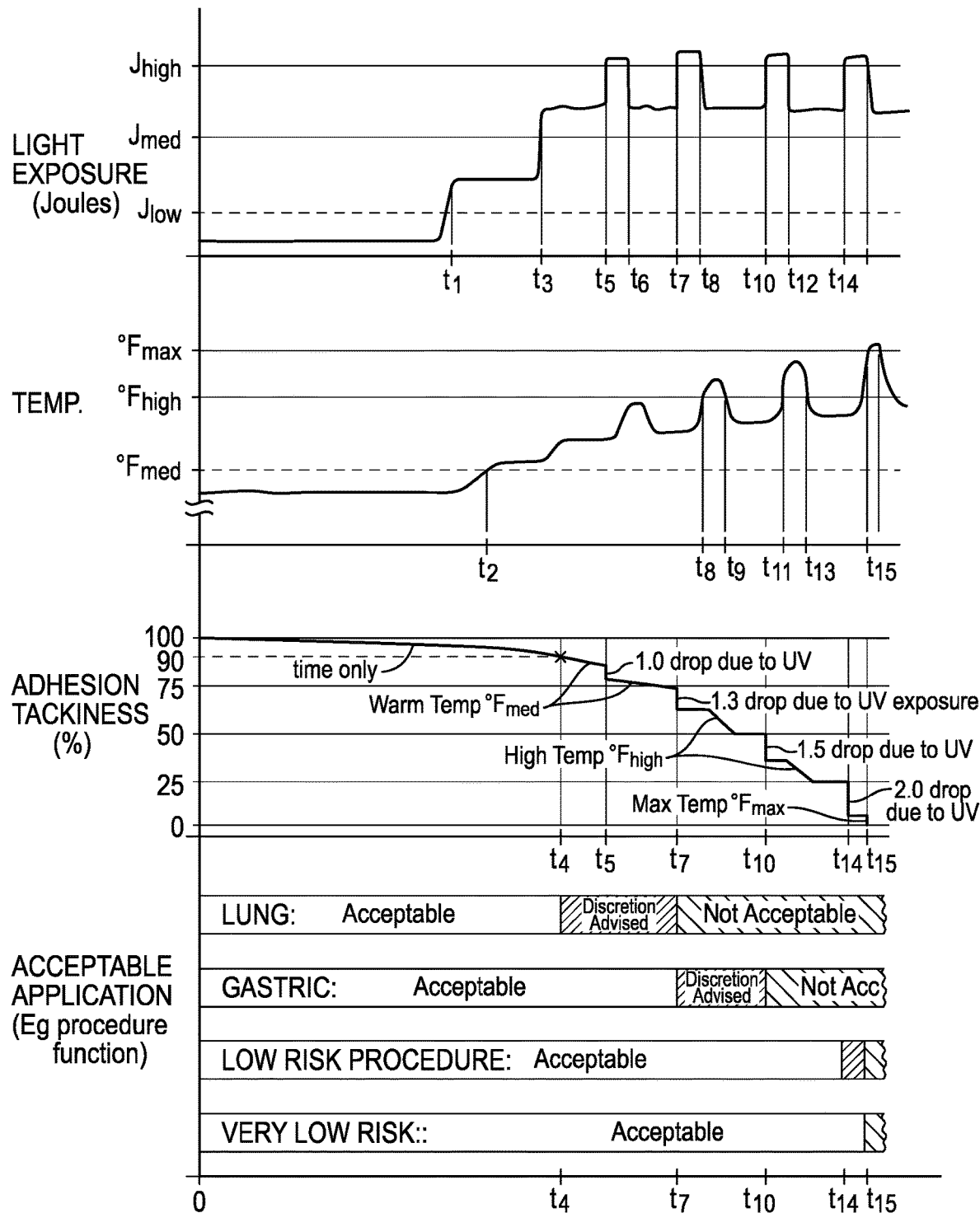
FIG. 17 is a graph showing exposure conditions, adhesion tackiness, and acceptable application over time.

Another embodiment of exposure condition data and processor analysis is shown in FIG. 17. In this illustrated embodiment, the processor is configured to determine indications and contraindications of an adjunct packaged by a packaging unit based on measurements of temperature and light. As discussed above, the adjunct has at least one medicant retained therein, and the packaging unit can package other components therein such as at least one cartridge body, one or more additional adjuncts, etc. As shown in FIG. 17, a sensor of the packaging unit, e.g., the sensor 4008 of FIG. 8, the sensor 4014 of FIG. 9, the sensor 4022 of FIG. 10, etc., can be configured to track temperature and light exposure over fifteen different time intervals (time zero to $t_{15}$). As mentioned above, the sensor can be a single sensor configured to monitor multiple exposure conditions or can be a plurality of sensors each configured to sense at least one of the exposure conditions. The following discussion is also applicable to other exposure conditions, e.g., ultraviolet, pressure, humidity, etc.

A memory operably coupled to the processor has predetermined thresholds stored therein for each of temperature and light similar to that discussed above regarding FIG. 16. In this illustrated embodiment, for temperature, the predetermined thresholds include a medium temperature $F_{med}$, a high temperature $F_{high}$, and a high temperature maximum $F_{max}$. A temperature range below the medium temperature $F_{med}$ is an acceptable temperature range for the adjunct in which the temperature will not adversely affect the adjunct's indications or contraindications. A temperature above the medium temperature $F_{med}$ and below the high temperature $F_{high}$ will degrade the adjunct at a first, medium level of degradation. A temperature above the high temperature $F_{high}$ and below the high temperature maximum $F_{max}$ will degrade the adjunct at a second, high level of degradation that is greater than the first level of degradation. A temperature above the high temperature maximum $F_{max}$ indicates that the adjunct has been exposed to an adverse enough temperature that the adjunct has been contraindicated and should not be used.

For light, the predetermined thresholds include a low light $J_{low}$, a medium light $J_{med}$, and a high light $J_{high}$. A light range below the low light $J_{low}$ is an acceptable light range for the adjunct in which the light will not adversely affect the adjunct's indications or contraindications. A light above the low light $J_{low}$ and below the medium light $J_{med}$ will degrade the adjunct at a first, low level of degradation. A light above the medium light $J_{med}$ and below the high light $J_{high}$ will degrade the adjunct at a second, medium level of degradation that is greater than the first level of degradation. A temperature above the high light $J_{high}$ indicates that the adjunct has been exposed to an adverse enough light that the adjunct has been contraindicated and should not be used. In this illustrated embodiment, the light range below the low light $J_{low}$ corresponds to darkness (no light exposure), light above the low light $J_{low}$ and below the medium light $J_{med}$ corresponds to indoor lighting exposure, light above the medium light $J_{med}$ and below the high light $J_{high}$ corresponds to indirect sunlight exposure, and light above the high light $J_{high}$ corresponds to direct sunlight exposure.

In general, FIG. 17 illustrates attachment adhesive degradation of the adjunct and its relationship to a surgical procedure in which the adjunct is planned to be used. The processor adjusts a durability threshold for the adjunct and compares the durability threshold to predetermined durability requirements of the surgical procedure. The comparison results in a data output of the processor that includes a recommendation or a change in the adjunct's usage status, procedure indications, or steps-of-use of the adjunct.

In this illustrated embodiment, the processor determines that the adjunct is acceptable for use in lung applications, gastric applications, low risk procedures, and very low risk procedures until time $t_4$. The data output of the processor would thus be "acceptable" for use of the adjunct. At time $t_4$, the adjunct has been experiencing a temperature above the medium temperature $F_{med}$ and below the high temperature $F_{high}$ since time $t_2$ and has been experiencing indoor lighting exposure since time $t_3$. The adjunct's adhesion tackiness has thus been reduced from 100% at time $t_2$ to 90% at time $t_4$. Adhesion tackiness of 90% is acceptable for gastric applications, low risk procedures, and very low risk procedures but is questionable for lung applications where tackiness has greater importance due to the particular importance of any leaks in the lung because of the adverse effect of leaks on breathing. The data output of the processor would thus be "acceptable" for use of the adjunct in gastric applications, low risk procedures, and very low risk procedures and "discretion advised" in lung applications. These indications and contraindications remain until time $t_7$, when the adjunct's exposures to light and temperature have reduced the adjunct's tackiness to 60%. Adhesion tackiness of 60% to 90% is acceptable for gastric applications, low risk procedures, and very low risk procedures but is questionable for lung applications. Adhesion tackiness below 60% is unacceptable for lung applications. The data output of the processor would thus be "unacceptable" for use of the adjunct in lung applications. Adhesion tackiness reducing to 60% does not change the adjunct's effectiveness for low risk procedures or very low risk procedures but does change the adjunct's effectiveness for gastric applications where the adjunct's tackiness may begin to be low enough to adversely affect proper gastric function with the adjunct implanted in the patient. The output of the processor would thus be "acceptable" for use of the adjunct in low risk procedures and very low risk procedures and "discretion advised" in gastric applications. These indications and contraindications remain until time $t_{10}$, when the adjunct's exposures to light and temperature have reduced the adjunct's tackiness to 40%. Adhesion tackiness below 40% is unacceptable for gastric applications. The data output of the processor would thus be "unacceptable" for use of the adjunct in gastric applications (as well as in lung applications, as above). Adhesion tackiness reducing to 40% does not change the adjunct's effectiveness for low risk procedures or very low risk procedures. The output of the processor would thus be "acceptable" for use of the adjunct in low risk procedures and very low risk procedures. These indications and contraindications remain until time $t_{14}$, when the adjunct's exposures to light and temperature have reduced the adjunct's tackiness to 25%. Adhesion tackiness reducing to 25% does not change the adjunct's effectiveness for very low risk procedures but does change the adjunct's effectiveness for low risk procedures. The output of the processor would thus be "acceptable" for use of the adjunct in very low risk procedures and "discretion advised" in low risk procedures. These indications and contraindications remain until time $t_{15}$, when the adjunct is exposed to a temperature above the high temperature maximum $F_{max}$. The adjunct is thus deemed unfit for use in any application. The output of the processor would thus be "unacceptable" for all procedures.

FIG. 16 and FIG. 17 are discussed with respect to exposure conditions' effect on an adjunct, but exposure conditions can be similarly processed for a medicant in addition to or instead of exposure conditions for an adjunct. An adjunct can therefore be determined to be unfit for use based the adjunct's exposure to one or more adverse exposure conditions and/or the medicant's exposure to one or more adverse exposure conditions.

Adjunct, Staple Cartridge, and Stapler Compatibility

In some instances, an adjunct and a medicant retained therein may not have experienced any exposure conditions that adversely affect their performance but may still be unsuitable for use. Compatibility can be determined in addition to exposure condition monitoring and analysis discussed above or can be determined without any exposure condition monitoring and analysis. Determining compatibility without any exposure condition monitoring and analysis may allow a packaging unit to be less costly and/or easier to manufacture since sensing capability need not be included.

In embodiments in which a staple cartridge is configured to be removably and replaceably coupled to an end effector of a surgical stapler, staples can only be fired out of the staple cartridge properly and/or safely if the staple cartridge is compatible with the surgical stapler. Staple cartridges have different sizes, so the staple cartridge removably and replaceably coupled to the end effector should have a size compatible with the particular end effector to which the staple cartridge is being coupled. Some surgical staplers may not be compatible with staple cartridges having an adjunct releasably coupled thereto, such as because the presence of the adjunct prevents the stapler's jaws from closing properly, because the presence of the adjunct prevents proper firing of staples because the stapler cannot provide sufficient force to drive the staples through the adjunct, because the cartridge is for a different kind of stapler (e.g., linear versus circular), and/or because the stapler's knife does not have sufficient sharpness and/or strength to cut the adjunct. It can therefore be important to establish compatibility between a surgical stapler and a staple cartridge having an adjunct releasably coupled thereto.

Establishing compatibility of a surgical stapler and a staple cartridge having an adjunct releasably coupled thereto generally involves determining whether the stapler, the staple cartridge, and the adjunct are predetermined to be suitable for use with one another. The establishment of compatibility before staples are attempted to be fired from the stapler may help ensure that the stapler and the adjunct can each function properly and/or help ensure that the patient is not injured or otherwise harmed by use of a stapler that includes a staple cartridge and/or adjunct that is incompatible therewith and should not be used with the stapler. In an exemplary embodiment, the compatibility is established before the staple cartridge is coupled to the stapler, e.g., before the staple cartridge is seated in the stapler's end effector, so as to necessarily be before the stapler attempts to fire staples from the staple cartridge.

In an exemplary embodiment, a method of establishing compatibility of a surgical stapler and a staple cartridge having an adjunct releasably coupled thereto includes a processor, e.g., of a surgical hub or other computer system, acquiring component data relating to the adjunct releasably coupled thereto from a packaging unit packaging the adjunct and comparing the component data with acceptable component data. The component data can be transmitted from the packaging unit using a communications interface of the packaging unit as discussed above, e.g., the communications interface transmitting stored data to an external device. In response to the component data not matching the acceptable component data, the processor can cause a warning to be provided indicating incompatibility. A user can thus be warned to not use incompatible components before attempting to use the components. A confirmation notification indicating compatibility can be provided in response to in response to the component data matching the acceptable component data. In some embodiments, the packaging unit packages the adjunct without the adjunct yet being releasably attached to the staple cartridge, with or without the packaging unit also packaging the adjunct. In other embodiments, the packaging unit packages the adjunct with the adjunct releasably attached to the staple cartridge, with the packaging unit not packaging the surgical stapler since the staple cartridge and the stapler being packaged together would indicate compatibility without component data comparison.

The method of establishing compatibility of a surgical stapler and a staple cartridge having an adjunct releasably coupled thereto may ensure that the correct staple cartridge and adjunct is utilized with the stapler. This may reduce a risk of inadvertently using unsuitable components that may lead to malfunction of the stapler, cartridge and/or adjunct, to improper or entirely absent staple deployment, and/or to incorrect implantation of the adjunct, each of which may be dangerous for the patient.

When a stapler is operated according to stored control parameters, establishing compatibility of components may ensure compatibility with the control parameters. For example, if the stapler has control parameters that indicate a maximum cutting element speed, establishing compatibility of components may ensure that the components are compatible with the cutting element speed and that, e.g., the adjunct will be cut as appropriate and will not unexpectedly tear or otherwise be unintentionally damaged in response to movement of the cutting element therethrough. The control parameters can be stored in a memory of the stapler or of an external device, and the comparison of whether the control parameters are suitable or need to be changed given the component data can be carried out by the processor.

The method can establish the compatibility of the stapler with only one of the cartridge and the adjunct releasably coupled to the adjunct or can establish the compatibility of the stapler with each of the cartridge and the adjunct releasably coupled to the adjunct. The stapler being compatible with only one of the cartridge and the adjunct releasably coupled to the adjunct can be indicative of the other of the cartridge and the adjunct releasably coupled to the adjunct being compatible with the stapler, e.g., because only certain size adjuncts can be used with certain size cartridges, because only certain adjuncts can be used with certain cartridges, etc.

Comparing the component data with the acceptable component data can include comparing component parameter(s), e.g., a number, a code, text, etc., of the component data with acceptable parameter(s), e.g., a number, a code, text, etc., of the acceptable component data stored at the external device that includes the processor and/or that is stored in a memory external to but accessible to the external device. The comparison includes determining whether each of one or more component parameters in the component data matches a corresponding parameter in the acceptable component data, with a match indicating compatibility and a mismatch indicating incompatibility. The acceptable component data can be stored, for example, in the form of a lookup table in which each possible component data receivable from a packaging unit is associated with acceptable staplers and/or cartridges. For another example, the acceptable component table can be stored as a lookup table that correlates adjuncts and/or staple cartridges usable with a particular surgical stapler to allow received component data to either be found in the table, indicating compatibility, or not found in the table, indicating incompatibility.

The acceptable component data can be updatable. Therefore, the suitability of the stapler with various cartridges and adjuncts can be updated based on developments in relation to the cartridge and adjunct and the stapler. For example, a lookup table stored in a memory of a surgical hub or other external device can be regularly updated with acceptable component data. For another example, an electronic instructions for user (eIFU) stored in a memory of a surgical hub or other external device can be regularly updated to include acceptable component data.

The component data stored at the packaging unit can include one or more component parameters. Examples of component parameters include adjunct manufacturer, adjunct model number, adjunct serial number, adjunct material, adjunct thickness, cartridge manufacturer, cartridge model number, cartridge serial number, and other parameters.

The component data can include an indication of compatible firing parameters. In this way, the first component data can indicate what one or more firing settings, e.g., motor speed, cutting element speed, tissue clamping force, etc., are suitable for operating with the component.

In addition to assessing the compatibility of the components, other approaches can be used for ensuring that only compatible devices are utilized. For example, a physical interface between the components can be sized and shaped to limit the physical compatibility to include components that are known to be compatible, such as by a staple cartridge and a jaw of an end effector having complementary mating features. In this way, the number of staple cartridges, and thus adjuncts releasably coupled to the cartridges, that are able to be coupled to the stapler is restricted and thereby reduces the possibility of utilizing non-compatible components.

In addition to component data, the packaging unit can be configured to transmit expiration date data to the external device that indicates an expiration date of the adjunct and/or of the medicant(s) retained by the adjunct. If the expiration date has passed based on a comparison with the current date, the processor can cause a warning to be provided indicating that the adjunct and/or medicant(s) have expired and that the adjunct should therefore not be used.

In addition to component data, the packaging unit can be configured to transmit sub-component data to the external device that indicates lot information for each packaged component, e.g., each adjunct, each medicant, each staple cartridge, each component part of the staple cartridge, etc. If any of the sub-component data indicates that a particular sub-component is faulty, based on a comparison with stored known faulty sub-component data, the processor can cause a warning to be provided indicating that the adjunct, the staple cartridge, the stapler, and/or medicant(s) should not be used and/or should be returned for maintenance or replacement. Comparing sub-component data may be useful if a lot of sub-components is found to be faulty but only some of the lot was incorporated into a small portion of a lot of end product, e.g., faulty staples used with only some staple cartridges in a lot, faulty cutting blade used with only some staple cartridges in a lot, faulty medicant used with only some adjuncts in a lot, etc., the recall could be targeted at just the devices that include the faulty sub-component. The processor can thus check to make sure that all components and sub-components are from good lots.

In some embodiments, the packaging unit is configured to transmit sub-component data but not component data. In some embodiments, the packaging unit is configured to transmit expiration date data but not component data. In some embodiments, the packaging unit is configured to transmit expiration date data and sub-component data but not component data. In some embodiments, the packaging unit is configured to transmit expiration date data and component data but not sub-component data. In some embodiments, the packaging unit is configured to transmit component data and sub-component data but not expiration date data.

Figure 18:
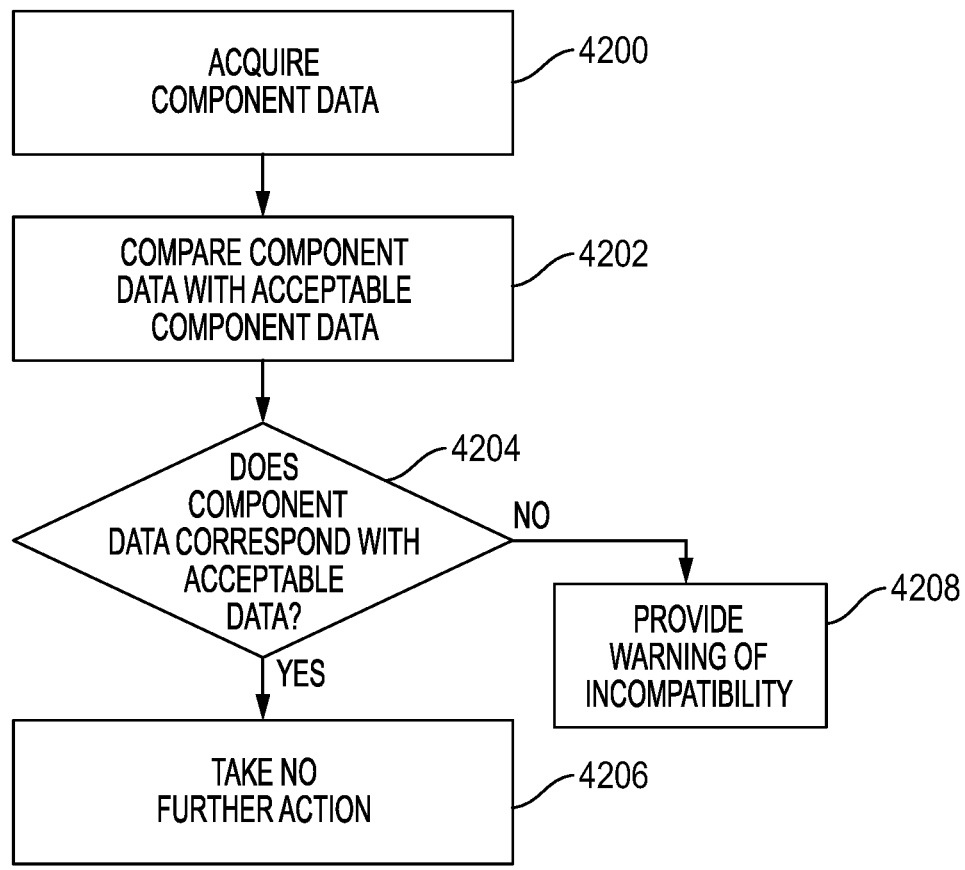
FIG. 18 is a flowchart of one exemplary embodiment of a method of establishing compatibility of components.

FIG. 18 illustrates an embodiment of a method of establishing compatibility of components. As shown, the component data is acquired 4200. As noted herein, the acquisition can occur by the component data being communicated from a packaging unit to an external device. The component data is then compared 4202 with acceptable component data. As noted herein, this comparison can be carried out using a processor, e.g., a processor of a surgical hub or other external device. The acceptable component data can be stored in a memory associated with the processor, and the processor can compare the acquired component data with the acceptable component data present in the memory. Based on this comparison, the processor determines 4204 whether the component data corresponds with the acceptable component data. In the situation that the component data is determined 4204 to correspond with the acceptable component data, the processor can take no further action 4206 since no incompatibility was detected. The relevant component can thus be used for staple and adjunct delivery. The processor can, however, provide a notification of compatibility. If the component data is determined 4204 to not correspond with acceptable first component data, then the processor causes 4208 a warning to be provided, as discussed herein, indicating incompatibility.

Figure 19:
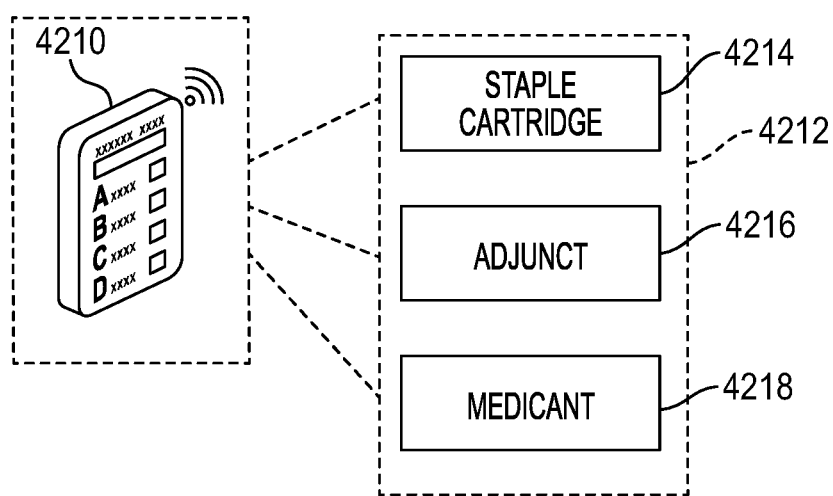
FIG. 19 is a schematic view of another embodiment of a communication network including another embodiment of a packaging unit and another embodiment of a computer system.

FIG. 19 illustrates an embodiment of a verification system including an external device 4210. The external device 4210 in this embodiment is in the form of a mobile phone configured to wirelessly interact with a packaging unit 4212, e.g., the packaging unit 4002 of FIG. 8, the packaging unit 4010 of FIG. 9, or other packaging unit. The packaging unit 4202 in this illustrated embodiment packages a staple cartridge 4214, an adjunct 4216, and a medicant 4218 releasably retained by the adjunct 4216. The staple cartridge 4214 can be packaged with the adjunct 4216 already releasably attached thereto. The external device 4210 is configured to acquire the component data, sub-component data, and/or expiration date data from the packaging unit 4202 as discussed herein and to analyze the received data as also discussed herein.

Packaging Unit Power

In some embodiments, a packaging unit can operate in a single power mode regardless of where the packaging unit is in its supply chain and whether or not the packaging unit has been opened. A sensor of the packaging unit can thus be "on" gathering data for an entire shelf life of the packaging unit, and a communications interface of the packaging unit can always have sufficient power to transmit data to an external device. Data may thus be assured of being gathered and communicated at all relevant times.

In other embodiments, a packaging unit can be configured to operate in a low power mode and in a high power mode. In the low power mode, a sensor of the packaging unit is provided with sufficient power from an on-board power source for the sensor to monitor data as discussed herein, and a communications interface of the packaging unit does not have sufficient power to transmit data to an external device. In the high power mode, the sensor and the communications interface are each provided with sufficient power. Less power is required from a power source for data gathering than for the data gathering in addition to allowing for data communication, so the low power mode may help conserve power and thereby help ensure that the power source has sufficient power throughout data communication in the high power mode. In an exemplary embodiment, opening the packaging unit is configured to move the packaging unit from the lower power mode to the high power mode. Until the packaging unit is opened, the packaging unit will continue to be potentially exposed to adverse exposure condition(s), so waiting until the packaging unit is opened to allow for data communication may help ensure that all relevant data is communication to an external device for analysis.

To facilitate movement from the low power mode to the high power mode, the packaging unit can include a tab configured to be automatically moved in response to opening of the packaging unit. Removing the tab fully "wakes up" the packaging unit's power source so the power source is providing power to the sensor to gather data (as in the low power mode) and to the communications interface to allow for data communication. The tab can be attached, for example, across a top box seam of a packaging unit and be configured to be automatically moved and/or broken when the box top is opened. For another example, the tab can be attached over a sealed opening of a foil pouch of a packaging unit and be configured to automatically moved and/or broken when the sealed opening is opened. The power source can include a first power source configured to provide power to the sensor in the low and high power modes and a second power source configured to only provide power to the communications interface in the high power mode. The tab can act as an insulator that prevents the second power source from providing power to the communications interface until the tab is removed, e.g., in response to the packaging unit being opened and causing the tab to move. In other words, the tab can be configured to prevent a circuit from being completed until the tab is removed. In some embodiments, the tab can include a conductive trace configured to facilitate circuit completion and prevention. Exemplary embodiments of tabs configured to be moved to cause movement from a low power mode to a high power mode are further described in Intl. Pat. App. No. PCT/IB2020/060710 entitled "Drug Delivery Device Sensing Modules" filed Nov. 13, 2020, which is hereby incorporated by reference in its entirety.

Instead of including a tab, a packaging unit can include a photosensor configured to facilitate movement of the packaging unit from a low power mode to a high power mode. The photosensor can be disposed in the packaging unit and not be exposed to light with the packaging unit unopened. With the packaging unit opened, the photosensor is exposed to light. The photosensor's exposure to light can trigger the packaging unit's power source to begin providing power to the packaging unit's communications interface.

In some embodiments, a packaging unit can be configured to move from a no power mode to a power on mode. In the no power mode, a communications interface of the packaging unit is not powered. In the power on mode, the communications interface is powered. The packaging unit is configured to be in the no power mode with the packaging unit in an unopened, closed state and to be in the power on mode with the packaging unit in an open state. The packaging unit is thus configured to move automatically from the no power mode to the power on mode in response to the packaging unit being opened, e.g., moving from the closed state to the open state. The packaging unit includes a power source configured to facilitate movement of the packaging unit from the no power mode to the power on mode. The power source is light sensitive. With the packaging unit in the closed state, the power source is dormant and not powered. The packaging unit being opened is configured to activate the power source by exposing the power source to light. The packaging unit is thus made of a material configured to prevent light passage therethrough to the power source inside of the packaging unit. The packaging unit is thus passive and unpowered until the packaging unit is opened. By not including an active power source such as a battery, the packaging unit may be disposed of in a safer and/or more environmentally friendly way than a packaging unit that includes an active power source.

In an exemplary embodiment, the packaging unit configured to move from the no power mode to the power on mode includes a degradable element configured to degrade in response to exposure to an environmental condition such as humidity, temperature, oxygen, or irradiation. In the power on mode, the communications interface is configured to communicate data indicative of a state of the degradable element to a surgical hub or other computer system, as discussed herein. The state of the degradable element corresponds to the degradable element's exposure to the environmental condition, thereby providing the surgical hub or other computer system exposure condition information that can be used as discussed herein.

Figure 20:
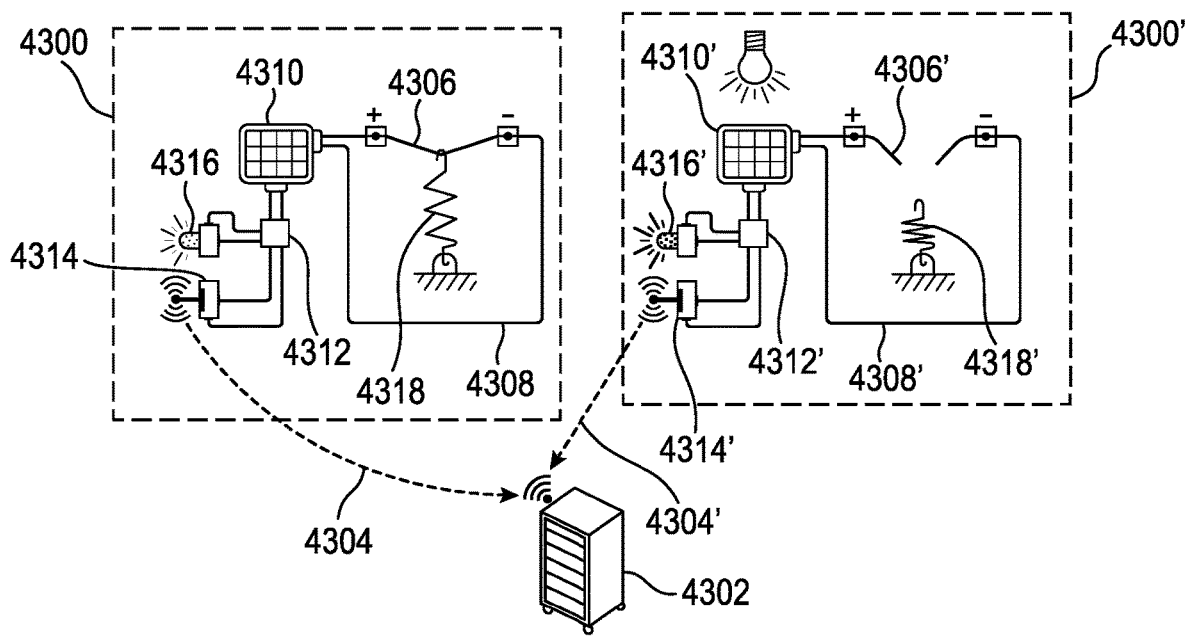
FIG. 20 is a schematic view of another embodiment of a communication network including another embodiment of a packaging unit and another embodiment of a surgical hub.

FIG. 20 illustrates an embodiment of a packaging unit 4300, 4300' configured to move from a no power mode to a power on mode. The no power mode is the initial, default mode. The packaging unit 4300, 4300' is shown communicating 4304, 4304' wirelessly with a surgical hub 4302 in this illustrated embodiment, but as discussed herein can communicate with another external device.

The packaging unit 4300, 4300' includes a degradable element 4306, 4306' configured to degrade in response to exposure to an environmental condition such as humidity (including moisture or water level), temperature, oxygen, or irradiation. The degradable element 4306 is thus generally configured as a sensor configured to monitor an exposure condition. The degradable element 4306 is intact in the no power mode. In other words, an initial state of the degradable element 4306 is non-degraded with the packaging unit 4300 in a closed state. A circuit 4308 that includes the degradable element 4306 is thus closed in the no power mode.

In the power on mode, the degradable element is either intact (non-degraded) or degraded. The packaging unit shown to the left of FIG. 20 as packaging unit 4300 illustrates the packaging unit in the power on mode with the degradable element 4306 intact. The circuit 4308 is thus closed in the power on mode with the degradable element 4306 not being degraded. The packaging unit shown to the right of FIG. 20 as packaging unit 4300', with use of hash marks for the elements corresponding to those same elements of the other illustrated packaging unit 4300, illustrates the packaging unit in the power on mode with the degradable element 4306' degraded. The circuit 4308' is thus open in the power on mode with the degradable element 4306' being degraded.

With the packaging unit 4300 in the no power mode, if the degradable element 4306 has been exposed to the environmental condition for a sufficient amount of time, e.g., because packaging unit 4300 has been in a high temperature environment long enough to degrade the degradable element 4306, because packaging unit 4300 has been in a high humidity environment long enough to degrade the degradable element 4306, because packaging unit 4300 has been in a high radiation environment long enough to degrade the degradable element 4306, because packaging unit 4300 has been exposed to oxygen long enough to degrade the degradable element 4306, etc., then the degradable element moves from being intact (degradable element 4306) to being degraded (degradable element 4306'), thereby moving the circuit from being closed (circuit 4308) to being open (circuit 4308').

The degradable element 4306, 4306' is made from an environmentally sensitive material. In an exemplary embodiment, the degradable element 4306, 4306' is conductive. The degradable element 4306, 4306' being conductive allows for the circuit 4308 to be closed with the degradable 4306 intact. The degradable element 4306, 4306' can be infused with or made from an absorbable polymer and doped conductive particles that are configured to degrade in the presence of the environmental condition it is set to monitor. When energized, the conductivity of the degradable element 4306, 4306' is directly proportional to the exposure the packaging unit 4300, 4300' has experienced. The degradable element 4306, 4306' can be infused with or made from a polymer that break down as fast or faster than the adjunct being monitored, e.g., than the adjunct packaged by the packaging unit 4300, 4300'. In an exemplary embodiment, as shown in FIG. 20, the degradable element 4306, 4306' includes a filament (either a single filament or a plurality of filaments) that forms a portion of the circuit 4308, 4308'.

The degradable element 4306, 4306' can be selected based on the adjunct and/or the medicant(s) packaged by the packaging unit 4300, 4300' so that the degradable element's susceptibility to one or more environmental conditions corresponds to or is more sensitive than the adjunct's and/or the medicant(s)' susceptibility to the one or more environmental conditions. The degradable element's susceptibility corresponding to the adjunct's and/or the medicant(s)' susceptibility allows the degradable element's degradation to correspond to effectiveness of the adjunct and/or the medicant(s). In this way, the degradable element degrading so as to no longer be intact can indicate that the adjunct and/or the medicant(s) should not be used. The degradable element's susceptibility being more sensitive than the adjunct's and/or the medicant(s)' susceptibility allows the degradable element's degradation to occur faster than a reduction in effectiveness of the adjunct and/or the medicant(s). The degradable element's degradation can thus lead the reduction in the effectiveness, which may help ensure that non-use of an ineffective adjunct and/or medicant(s).

The packaging unit 4300, 4300' also includes light sensitive element 4310, 4310' in the circuit 4308, 4308'. The light sensitive element 4310, 4310' is in series with the degradable element 4306, 4306'. With the packaging unit 4300, 4300' in the power on mode (with the degradable element 4306, 4306' degraded or non-degraded), the light sensitive element 4310, 4310' is configured to provide power to a controller 4312, 4312' of the packaging unit 4300, 4300', to a communications interface 4314, 4314' of the packaging unit 4300, 4300', and to a light 4316, 4316' of the packaging unit 4300. The light sensitive element 4310, 4310' thus serves as a power source. In the no power mode, the light sensitive element 4310 does not provide power to any of the controller 4312, the communications interface 4314, and the light 4316.

The light sensitive element 4310, 4310' is configured to begin providing power to the controller 4312, 4312', the communications interface 4314, 4314', and the light 4316, 4316' in response to being exposed to light. Thus, the opening of the packaging unit 4300, 4300', e.g., moving from the closed state to the open state, is configured to activate the light sensitive element 4310, 4310' by allowing the light sensitive element 4310, 4310' to become exposed to light, either artificial light, sunlight, or both artificial light and sunlight, in a room in which the packaging unit is opened. In an exemplary embodiment, the light sensitive element 4310, 4310' includes a solar cell (either a single solar cell or a plurality of solar cells).

The communications interface 4314, 4314' includes a wireless transmitter in this illustrated embodiment and is configured to communicate wirelessly with the surgical hub 4302 with the communications interface 4314' being powered by the light sensitive element 4314'. Data communicated to the surgical hub 4302 using the communications interface 4314' regards a state of the degradable element 4306'. With the degradable element 4306' being conductive, a conductivity of the degradable element 4306' is proportional to an amount of degradation of the degradable element 4306', e.g., a resistance of the conductive degradable element 4306' changing based on its amount of degradation. The data communicated by the communications interface 4314' can thus include an amount of degradation of the degradable element 4306'. The communications interface 4314 cannot wirelessly communicate with the surgical hub 4302 (or with anything else) with the packaging unit 4300 in the no power mode. The controller 4312, 4312' is configured to control the communications interface 4314, 4314' based on the sensed condition of the circuit 4308, 4308'. With the circuit 4308 being closed, the controller 4312 is configured to cause the communications interface 4314 to communicate to the surgical hub 4302 that the packaging unit 4300, and thus its packaged components, meets quality standards, e.g., because the packaging unit 4300 has not experienced an adverse environmental condition indicative of ineffective adjunct and/or ineffective medicant. With the circuit 4308' being open, the controller 4312' is configured to cause the communications interface 4314' to communicate to the surgical hub 4302 that the packaging unit 4300', and thus its packaged components, does not meet quality standards, e.g., because the packaging unit 4300' has experienced an adverse environmental condition indicative of ineffective adjunct and/or ineffective medicant. Such an unmet quality standards communication can cause the surgical hub 4302 to provide a warning, as discussed herein.

The light 4316, 4316' includes a single LED in this illustrated embodiment but can include another type of light and/or a plurality of lights. In the no power mode, the light 4316 is off (not illuminated). In the power on mode, the light 4316, 4316' is on (illuminated). The light 4316, 4316' being on thus provides a visual indication that the packaging unit 4300, 4300' is open and is in the power on mode. A color of the light's illumination in the power on mode depends on whether or not the degradable element is degraded (degradable element 4306') or intact (degradable element 4306). In this illustrated embodiment, the light 4316 is illuminated in green with the degradable element 4306 intact, and the light 4316' is illuminated in red with the degradable element 4306' degraded, but other colors can be used. In other embodiments, instead of being different colors, the light 4316' can be continuously illuminated when the degradable element is degraded (degradable element 4306'), and the light 4316 can be blinking when the degradable element is not degraded (degradable element 4306). Alternatively, the light 4316' can be blinking when the degradable element is degraded (degradable element 4306'), and the light 4316 can be continuously illuminated when the degradable element is not degraded (degradable element 4306).

The controller 4312, 4312' is configured to sense whether the circuit is closed (circuit 4308, degradable element 4306 not degraded) or open (circuit 4308', degradable element 4306' degraded). The controller 4312, 4312' is configured to control the light 4316, 4316' based on the sensed condition of the circuit 4308, 4308'. For example, as shown in this illustrated embodiment, the controller 4312, 4312' causes the light 4316 to illuminate in green with the circuit 4308 being closed and causes the light 4316' to illuminate in red with the circuit 4308' being open.

As in this illustrated embodiment, the packaging unit 4300, 4300' can include a force element 4318, 4318', e.g., a coil spring, an elastic filament, or other force element, configured to provide a force to the degradable element 4306 with the packaging unit 4300 in the no power mode. The force element 4318, 4318' is configured to facilitate breakage of the intact degradable element 4306 that has been weakened by exposure to the environmental condition. The force element can thus help ensure that the circuit 4308' is open with the degradable element 4306' degraded. The force element 4318, 4318' is not conductive, such as by being formed of a non-conductive material and/or having an insulative coating, so as to not form a part of the circuit 4308, 4308'.

Figure 21:
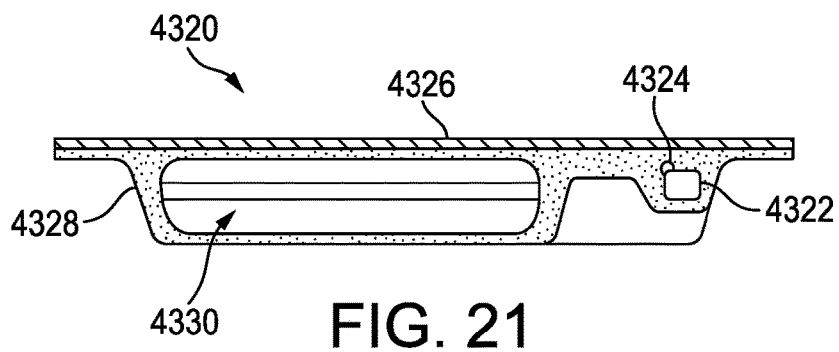
FIG. 21 is a longitudinal cross-sectional view of another embodiment of a packaging unit with a cover of the packaging unit closed.
Figure 22:
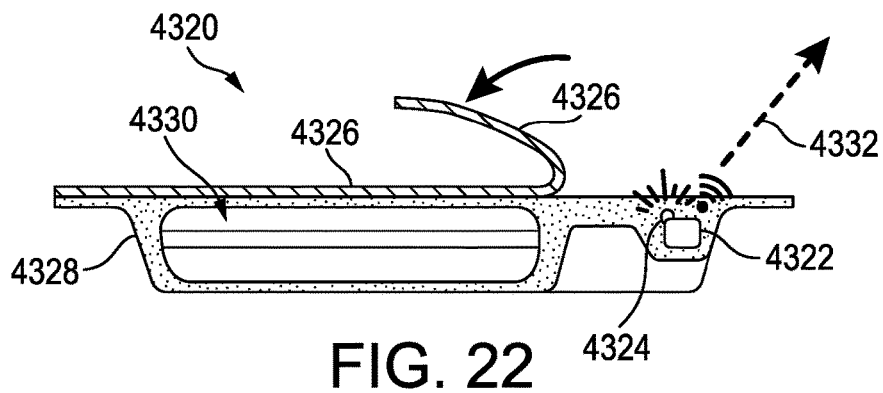
FIG. 22 is a longitudinal cross-sectional view of the packaging unit of FIG. 21 with the cover of the packaging unit open.

FIG. 21 and FIG. 22 illustrate another embodiment of a packaging unit 4320 configured to move from a no power mode to a power on mode. The packaging unit 4320 is generally configured and used similar to the packaging unit 4300, 4300' of FIG. 20 discussed above, e.g., includes a degradable element (obscured in FIG. 21 and FIG. 22), a circuit (obscured in FIG. 21 and FIG. 22), a light sensitive element 4322, a controller (obscured in FIG. 21 and FIG. 22), a communications interface 4322, a light 4324, and a force element (obscured in FIG. 21 and FIG. 22). As shown in FIG. 21 and FIG. 22, the light sensitive element and the communications interface are integrated together in this illustrated embodiment. The light sensitive element 4322 in this illustrated embodiment includes a solar cell (either a single solar cell or a plurality of solar cells). The communications interface 4322 in this illustrated embodiment includes a wireless transmitter.

The packaging unit 4320 in this illustrated embodiment includes a foil pouch having a cover 4326. The cover 4326 is configured to be manually removed (fully or partially) from a housing 4328 of the packaging unit 4320 that houses packaged elements in a cavity 4330 thereof. The packaged elements are not shown in FIG. 21 and FIG. 22 but can include elements as discussed herein, e.g., an adjunct releasably retaining medicant(s) therein, a plurality of adjuncts each releasably retaining a medicant therein, a staple cartridge having an adjunct releasably attached thereto with the adjunct releasably retaining medicant(s) therein, a plurality of staple cartridges each having an adjunct releasably attached thereto with the adjunct releasably retaining medicant(s) therein, etc. As discussed herein, the packaging unit 4320 can be packaged in a bulk packaging unit and removed therefrom for use.

As shown in FIG. 21 and FIG. 22, the light sensitive element 4322, the communications interface 4322, and the light 4324 can be embedded in the housing 4328. The obscured degradable element, circuit, controller, and force element are similarly embedded in the housing 4328. Embedding these elements in the housing 4328 may help protect the elements from being damaged during the packaging unit's progression through the supply chain.

FIG. 21 illustrates the packaging unit 4320 in the no power mode. The cover 4326 is thus closed, such that the light sensitive element 4322 is not exposed to light. The light 4324 is off. The degradable element is subject to environmental conditions in the no power mode and is thus able to degrade if warranted.

FIG. 22 illustrates the packaging unit 4320 in the power on mode. The cover 4326 is thus open, such that the light sensitive element 4322 is exposed to light. The light 4324 is on. A color (and/or a blinking/continuous illumination state) of the illuminated light 4324 depends on whether or not the degradable element is degraded or intact, as discussed above. Now receiving power from the light sensitive element 4322 with the packaging unit 4320 in the power on mode, the communications interface 4322 is shown transmitting 4332 data regarding a state of the degradable element to a surgical hub or other computer system as discussed above.

In some embodiments, instead of a packaging unit that is configured to move from a no power mode to a power on mode including a light sensitive element configured to provide power to elements of the packaging unit, the packaging unit can include a magnetic-field powered element such as an RFID tag or other passively magnetically powered element. The magnetic-field powered element is configured to only be powered when in the presence of a magnetic field. Thus, when exposed to a magnetic field, such as that provided by an RFID reader or other device, the magnetic-field powered element can allow a communications interface of the packaging unit to communicate data as discussed above.

Post-Implantation Adjunct Monitoring

As discussed above, an adjunct can be absorbable. The adjunct can thus be configured to degrade in a patient's body. The adjunct's absorbable configuration can be exploited to help monitor the patient's healing. Monitoring the adjunct's breakdown (generally referred to herein as the adjunct "degrading") in the patient's body after the adjunct has been implanted can serve as a means to monitor the patient's healing. The adjunct's degradation generally corresponds to the patient's healing since tissue heals over time and since any medicants releasably retained by the adjunct are releasable over time after the adjunct has been implanted in the patient's body. Monitoring the adjunct's degradation may therefore allow for assessment of the patient's healing.

The adjunct's monitoring can occur non-invasively from outside the patient's body. The patient therefore does not need any surgical intervention to assess the adjunct's absorption state and the patient's healing after the adjunct has been implanted.

An implanted adjunct's degradation can be monitored in a variety of ways. For example, the monitoring can include imaging the adjunct for visualization of radio-opaque markers releasable from the adjunct in the body of the patient. For another example, the monitoring can include tracking a waste byproduct of the adjunct that is releasable from the implanted adjunct into the body of the patient. For yet another example, the monitoring can include monitoring waste of the patient. For still another example, in embodiments in which the adjunct is delivered using a surgical stapler, the monitoring can include tracking a trackable element delivered to the patient from a surgical stapler that stapled the adjunct in the patient. Each of these examples is discussed further below.

Information gathered regarding the implanted adjunct's degradation can be communicated to a surgical hub or other computer system, such as via a communications interface of a device that gathers images, trackable material data, etc. as discussed further below. The surgical hub or other computer system can be configured to provide a notification of the adjunct's monitoring to the patient's surgeon or other medical care professional(s), similar to that discussed above regarding providing a notification of compatibility, to facilitate the patient's treatment.

In some embodiments, monitoring an implanted adjunct's breakdown in a patient's body can include imaging the adjunct for visualization of radio-opaque markers releasable from the adjunct in the body of the patient. In such embodiments, the radio-opaque markers are retained by the adjunct when the adjunct is implanted, similar to that discussed herein regarding the adjunct releasably retaining a medicant when the adjunct is implanted. As the adjunct breaks down and is bioabsorbed, the radio-opaque markers will be moved from their original implanted location where the adjunct was stapled or otherwise attached to the patient. The adjunct's degradation, and thus patient healing, can thereby be monitored.

The patient can be imaged at a plurality of different times, e.g., a plurality of different days sequential with one another and/or separated by one or more days, for visualization of the radio-opaque markers. The adjunct's degradation can thus be monitored over time, with each subsequent imaging providing an updated indication of the patient's healing. Comparing each of the images can thus provide an indication of the radio-opaque markers' movement in the patient's body over time and, thus, the adjunct's degradation and the patient's healing over time.

In embodiments in which an adjunct is compressible, such as by being a tissue thickness compensator, a comparison of images taken over time can show if the adjunct is breaking down such that the radio-opaque markers are moving closer together as the adjunct degrades or are moving apart from one another as the adjunct holding them constrained degrades and the radio-opaque markers are free to migrate.

The radio-opaque markers can be formed from any of a variety of biocompatible radio-opaque materials and can be releasably retained by the adjunct in a variety of ways. For example, in embodiments in which the adjunct is formed from a foam, the radio-opaque markers can be embedded throughout the foam such that, as the foam degrades, the radio-opaque markers are released. Any medicants releasably retained by the foam adjunct are similarly releasable, as discussed herein. For another example, in embodiments in which the adjunct is formed from a fibrous structure, the radio-opaque markers can be trapped between fibers forming the fibrous structure such that, as the fibrous structure degrades, the radio-opaque markers are released. Any medicants releasably retained by the fibrous structure adjunct are similarly releasable, as discussed herein.

In an exemplary embodiment, the radio-opaque markers are independent elements from the adjunct and the medicant(s) retained by the adjunct, as well as from device(s) that facilitate the delivery of the adjunct and medicant(s) to tissue, such as a surgical stapler that applies the staples and the adjunct. Existing adjuncts and existing medicants thus do not need to be modified, nor do future adjuncts or medicants need to be particularly designed, in order to be used with radio-opaque markers as discussed herein.

Figure 23:
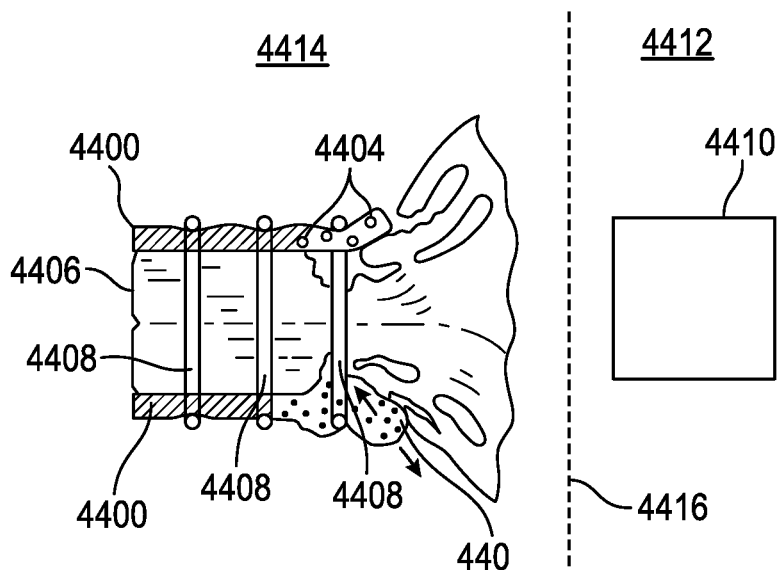
FIG. 23 is a perspective view of an imaging system located outside of a body of a patient and another embodiment of an adjunct stapled inside the patient.

FIG. 23 illustrates an embodiment of an adjunct 4400 releasably retaining a medicant 4402 and a plurality of radio-opaque markers 4404. The adjunct 4400 is retaining a single medicant 4402 but as discussed herein can retain a plurality of medicants. In this illustrated embodiment, the adjunct 4400 is configured to change conformation.

FIG. 23 shows the adjunct 4400 implanted at an edge of a tissue 4406 of a patient by deployment of staples 4408 deployed into the tissue 4406. With the adjunct 4400 implanted in the patient, the patient can be imaged using an imaging system 4410, such as a fluoroscopy system, an x-ray system, or other system, that is configured to provide an image allowing visualization of the radio-opaque markers 4404. The imaging system 4410 is located outside 4412 the patient's body, and the adjunct 4400, the medicant 4402, and the radio-opaque markers 4404 are located inside 4414 the patient's body. The imaging system 4410 is thus configured to image the patient from outside 4410 the patient's body. An external surface of the patient is schematically represented by a dotted line 4416. Each image taken using the imaging system 4410 can be taken at a location of known adjunct 4400 implantation, which in this illustrated embodiment is at the edge of the tissue 4406, or a plurality of images at two or more different locations can be taken using the imaging system 4410. One or more of the two or more locations can include the location of known adjunct 4400 implantation. Taking at least one image at the location of known adjunct 4400 implantation may allow for the monitoring of healing of the tissue 4406 at the location of known adjunct 4400 implantation. Taking at least one image that does not include the location of known adjunct 4400 implantation may allow for the monitoring of healing away from the location of known adjunct 4400 implantation, either at the tissue 4406 or other location. Healing away from the location of known adjunct 4400 implantation can be caused by the medicant 4402 moving within the patient's body. Taking at least one image that does not include the location of known adjunct 4400 implantation may allow for monitoring of how the degrading adjunct 4400 and/or the released medicant 4402 moves in the patient's body, which may help facilitate post-operative analysis useful for the patient and/or future patients who receive a similar adjunct and/or similar medicant.

Figure 24:
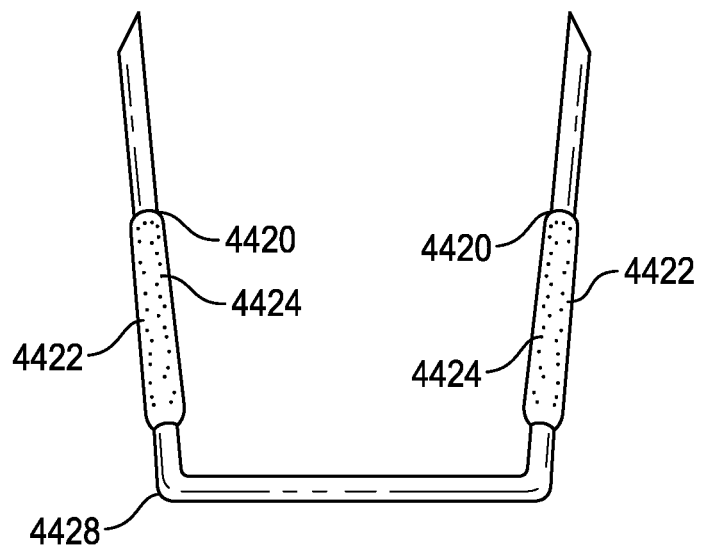
FIG. 24 is a perspective view of one exemplary embodiment of a staple having an adjunct disposed thereon.
Figure 25:
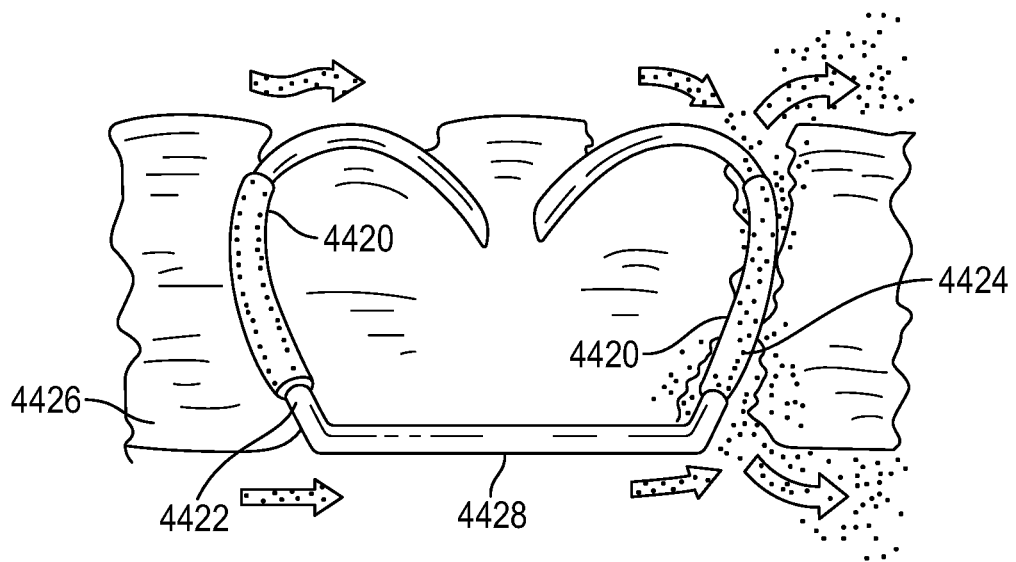
FIG. 25 is a partial cross-sectional side view of the staple of FIG. 24 applied to tissue.

FIG. 24 and FIG. 25 illustrate another embodiment of an adjunct 4420 releasably retaining a medicant 4422 and releasably retaining a plurality of radio-opaque markers 4424. FIG. 24 illustrates the adjunct 4420 before implantation, and FIG. 25 illustrates the adjunct 4420 implanted in a body of a patient with the adjunct 4420 stapled to tissue 4426 of the patient. In this illustrated embodiment, a surgical staple 4428 includes the adjunct 4420 disposed over each leg of the staple 4428 configured to be used in delivering the adjunct 4420 to the tissue 4426. The adjunct 4420 is thus a two-part adjunct in this illustrated embodiment with each part of the adjunct 4420 releasably retaining the medicant 4422 and the radio-opaque markers 4424. In other embodiments, one part of the adjunct 4420 can releasably retain the medicant 442, and the other part of the adjunct 4420 can releasably retain the radio-opaque markers 4424. In some embodiments, only one staple leg can have an adjunct thereon, or one or both staple legs can have more than one adjunct thereon.

Figure 26:
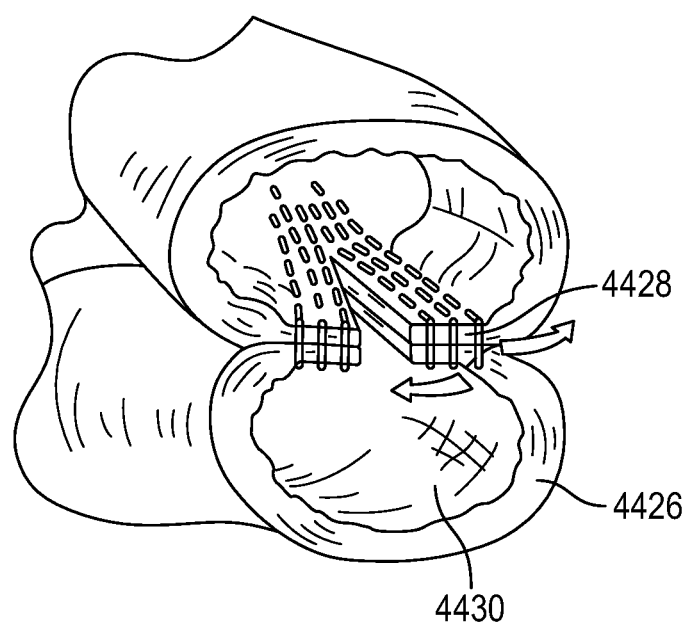
FIG. 26 is a perspective, zoomed-out view of the tissue of FIG. 25 having the staple and a plurality of additional staples applied thereto.

The medicant 4422 and the radio-opaque markers 4424 are configured to be released from the adjunct 4420 when the staple 4428 is deformed upon deployment of the staple 4428 into the tissue 4426 of a patient, e.g., a bowel, a lung, etc., as shown in FIG. 25. Some of the medicant 4422 and/or some the radio-opaque markers 4424 can remain in the adjunct 4420 upon stapling and be released from the adjunct 4420 as the adjunct 4420 degrades. FIG. 26 shows the staple 4428 and a plurality of additional similar staples each also having an adjunct disposed thereon similar to the disposal of the adjunct 4420 on the staple 4428. FIG. 26 illustrates a side-to-side anastomosis, but the staple 4428 can be used in other surgical procedures. The medicant 4222 and/or the radio-opaque markers 4424 can be released from the adjunct 4420 into a passageway 4430 extending through the tissue 4426. Imaging the passageway at the location of the adjunct's implantation at the tissue 4426 and/or away from the location of the adjunct's implantation at the tissue 4426 may thus allow for visualization of the radio-opaque markers 4424.

In some embodiments, monitoring an implanted adjunct's breakdown in a patient's body can include tracking a waste byproduct of the adjunct that is releasable from the implanted adjunct into the body of the patient. In such embodiments, the adjunct includes the waste byproduct releasable from the implanted adjunct into the body of the patient. Similar to that discussed above regarding radio-opaque markers releasable from an adjunct, as the adjunct releasably retaining the waste byproduct breaks down and is bioabsorbed, the waste byproduct will be moved from their original implanted location where the adjunct was stapled or otherwise attached to the patient. The adjunct's degradation, and thus patient healing, can thereby be monitored.

The waste byproduct can be formed from any of a variety of biocompatible materials. For example, the adjunct can be formed from an absorbable material and a non-absorbable material. The non-absorbable material, such as a non-absorbable polymer, can define the waste byproduct. As the absorbable material of the adjunct breaks down in a patient's body, the waste byproduct will be released from the adjunct to allow for monitoring of the waste byproduct. The adjunct can be formed from the absorbable material and the non-absorbable material in a variety of ways, such as by the adjunct formed from a fibrous structure that includes a plurality of absorbable fibers and a plurality of non-absorbable fibers, the adjunct formed from at least one absorbable film attached to at least one non-absorbable film, or other adjunct configuration. For another example, the waste byproduct can include a ferrous material configured to be detected by a metal detector. The adjunct can include the ferrous material similar to that discussed above regarding an adjunct including radio-opaque markers. For another example, the waste byproduct can include a radioactive material configured to be detected by a radiation detector. The adjunct can include the radioactive material similar to that discussed above regarding an adjunct including radio-opaque markers. The radioactive material is slightly radioactive so as to be a safe level. For yet another example, the waste byproduct can include a physiologic bi-product. For still another example, the waste byproduct can include a metabolism marker or degradation decomposition product. As mentioned above, an adjunct can be formed from an absorbable polymer. Absorbable polymers tend to break down into sub components, including a component that is metabolized by the body and another component that is not metabolized by the body and is released from the body as waste. The component that is not metabolized can be the waste byproduct. As one example, with PLGA, metabolized product can include a material that acts as a sugar and waste byproduct including lactic acid and glycolic acid excreted by the kidneys. As another example, with PLA, metabolized product can include a material that acts as a sugar and waste byproduct including lactic acid excreted by the kidneys.

The waste byproduct can be monitored locally using a monitoring device. The monitoring device can be configured to monitor a concentration and a location of the waste product in a patient's body. The monitoring device is located outside of the patient's body similar to that discussed above regarding the imaging system 4410 of FIG. 23 that is configured to monitor a material released from an implanted adjunct. In an exemplary embodiment, the monitoring device is a wearable monitor, which may allow a patient to be easily and non-invasively monitored.

In some embodiments, the waste byproduct can include a ferrous material, and the monitoring device can include a metal detector configured to monitor a concentration and a location of the ferrous material in a patient's body. At time zero when the adjunct releasably retaining the ferrous material is implanted in the patient's body, the concentration of the ferrous material would be known. The monitoring device can then track any changes to this concentration or dispersion of the ferrous material away from the site of implantation.

In some embodiments, the waste byproduct can include a radioactive material, and the monitoring device can include a radiation detector configured to monitor a concentration and a location of the radioactive material in a patient's body. At time zero when the adjunct releasably retaining the radioactive material is implanted in the patient's body, the concentration of the radioactive material would be known. The monitoring device can then track any changes to this concentration or dispersion of the radioactive material away from the site of implantation.

In some embodiments, monitoring an implanted adjunct's breakdown in a patient's body can include monitoring waste of the patient. An adjunct can be implanted at a variety of locations in a patient, such as at a lung, a gastrointestinal tract, or a liver. In situations where the adjunct is implanted at a gastrointestinal tract, such as at a colon, the adjunct's location can be exploited to facilitate monitoring of the adjunct's degradation in the patient's body. In such situations, the adjunct's waste byproduct can be released into a passageway of the gastrointestinal tract similar to that discussed above regarding release of the radio-opaque markers 4424 of FIG. 26 being released from the adjunct 4420 into the passageway 4430.

Monitoring the waste of the patient can include tracking a waste byproduct of the adjunct that is releasable from the implanted adjunct into the body of the patient and released with the waste. In such embodiments, the waste byproduct can be monitored systemically after the waste byproduct has exited the patient as waste. The waste byproduct can thus be monitored from outside of the patient's body. The waste byproduct that is monitored after its release from a patient's body can include a metabolism marker or degradation decomposition product.

A toilet can include a smart computer system monitor, similar to a urinal puck, that is configured to track the metabolism marker or degradation decomposition product. The smart monitor can be configured to provide a notification of the adjunct's monitoring to the patient's surgeon or other medical care professional(s), or the smart monitor can be configured to communicate data gathered thereby to a surgical hub or other computer system configured to provide such a notification.

In addition to or in alternative to using a smart monitor, a patient's feces can be collected for detection of the waste byproduct in the feces. The waste byproduct can be detected in the feces in any of a variety of ways, such as by the waste byproduct including a dye that, if present in the waste, will be visually observable. For another example, the waste byproduct can include a reactive chemical that, if present in the waste, will react with a reactor, such as litmus paper or an activator chemical, applied to the feces. Thus, pH can be used to detect the waste byproduct. Bacterial load or other mineral reactors could also be used.

In some embodiments, monitoring an implanted adjunct's breakdown in a patient's body can include tracking a trackable element delivered to the patient from a surgical stapler that stapled the adjunct in the patient. In situations where an adjunct is implanted at a gastrointestinal tract, such as at a colon, the adjunct's location can be exploited to facilitate monitoring of the adjunct's degradation in the patient's body. In such situations, the trackable element can be released into a passageway of the gastrointestinal tract similar to that discussed above regarding release of the radio-opaque markers 4424 of FIG. 26 being released from the adjunct 4420 into the passageway 4430. The trackable element can be configured to interact with a microbiome of the gastrointestinal tract, such as at a colon. A tracked magnitude of the release of the tracking element can be used as a means to analyze a balance of the intestinal micro biome and/or the healing response over time. Parameters within the colon that can be used as an interactive measure linked to the microbiome balance or healing include pH, $O_2$, and $CO_2$. $CO_2$ concentrations cause a shift in pH in organic structures. Additional testing may be done if increased pH is detected in order to determine the source of the pH change, which could lead to a $O_2/CO_2$ balance measure. Different bacteria use $O_2$ and $CO_2$ differently and some excrete them. The balance measure can indicate the bacterial load of the gut and therefore shed light on the balance of good bacteria to bad bacteria in the microbiome.

In an exemplary embodiment, the trackable element is delivered to the patient separately from the adjunct. Each of the trackable element and the adjunct can be delivered to the patient using a same device, e.g., a surgical stapler as discussed herein, but can each be delivered separately from the device. Adjuncts thus need not be modified in order to be used with a trackable element.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical system, comprising:
  a bioabsorbable adjunct configured to be implanted in a body of a patient using a surgical stapler;
  a medicant releasably retained by the adjunct and configured to be released from the adjunct into the body of the patient;
  a packaging unit packaging the adjunct and the medicant;
  a sensor configured to, with the packaging unit packaging the adjunct and the medicant, gather data regarding an exposure condition of at least one of the adjunct and the medicant, the exposure condition being a condition that affects performance of at least one of the adjunct in the body of the patient and the medicant in the body of the patient; and a processor configured to
receive the data gathered by the sensor,
determine a recommendation of use of the adjunct and the medicant in a surgical procedure based on the received data and on a requirement of the surgical procedure, and
cause notice of the recommendation to be provided to a medical practitioner associated with the surgical procedure.

2. The system of claim 1, wherein the recommendation includes a recommended shelf-life of the adjunct and the medicant.

3. The system of claim 1, wherein the recommendation includes at least one of a recommended contraindication and a recommended indication of the adjunct and the medicant.

4. The system of claim 1, wherein the recommendation includes a recommended shelf-life of the adjunct and the medicant that is based at least on the gathered data regarding the exposure condition; and
the recommendation includes at least one of a recommended indication and a recommended contraindication of the adjunct and the medicant, the at least one of the recommended indication and the recommended contraindication is based at least on the requirement of the surgical procedure.

5. The system of claim 1, wherein the recommendation includes a recommended time after opening of the packaging unit within which the adjunct should be implanted in the body of the patient in the surgical procedure.

6. The system of claim 1, wherein the requirement of the surgical procedure is specific to a threshold adjunct durability for a type of the surgical procedure; and
determining the recommendation includes comparing the threshold adjunct durability with a durability of the adjunct as indicated by the gathered data regarding the exposure condition.

7. The system of claim 1, wherein the environmental condition includes at least one of light and temperature.

8. The system of claim 1, wherein the environmental condition includes at least one of humidity, oxygen, time, light, vibration, and atmospheric pressure.

9. The system of claim 1, wherein the packaging unit includes the sensor.

10. The system of claim 1, wherein a surgical hub includes the processor, the surgical hub being external to the packaging unit and being configured to electronically communicate with a cloud-based computer system that is configured to communicate with at least one additional surgical hub.

11. A surgical method, comprising:
receiving at a computer system external to a packaging unit, from a communications interface of the packaging unit packaging a bioabsorbable adjunct that releasably retains a medicant therein and that is configured to be implanted using a surgical stapler, data gathered by a sensor of the packaging unit indicative of an exposure condition of the packaging unit, the exposure condition being a condition that affects performance of at least one of the adjunct in a patient and the medicant in the patient;
determining, at the computer system, a recommendation of use of the adjunct and the medicant in a surgical procedure based on
the received data indicative of the exposure condition, and
a requirement of the surgical procedure; and
providing notice of the recommendation to a medical practitioner associated with the surgical procedure.

12. The method of claim 11, wherein the recommendation includes a recommended shelf-life of the adjunct and the medicant.

13. The method of claim 11, wherein the recommendation includes a recommended indication of the adjunct and the medicant.

14. The method of claim 11, wherein the recommendation includes a recommended contraindication of the adjunct and the medicant.

15. The method of claim 11, wherein the recommendation includes a recommended time after opening of the packaging unit within which the adjunct should be implanted in the body of the patient in the surgical procedure.

16. The method of claim 11, wherein the requirement of the surgical procedure is specific to a threshold adjunct durability for a type of the surgical procedure; and
determining the recommendation includes comparing the threshold adjunct durability with a durability of the adjunct as indicated by the gathered data regarding the exposure condition.

17. The method of claim 11, wherein the requirement of the surgical procedure is specific to at least one of a patient on which the surgical procedure is to be performed and a surgeon to perform the surgical procedure.

18. The method of claim 11, wherein the packaging unit and the adjunct packaged therein are sterile prior to the packaging unit being opened and are not sterile after the packaging unit has been opened;
the method further comprises gathering the data, using the sensor of the packaging unit, prior to opening of the packaging unit; and
the method further comprises transmitting, using a communications interface of the packaging unit, the data to be received at the computer system.

19. The method of claim 11, wherein the environmental condition includes at least one of light, temperature, humidity, oxygen, time, light, vibration, and atmospheric pressure.

20. The method of claim 11, wherein the surgical procedure is to be performed on the patient, and the requirement of the surgical procedure is specific to a type of the surgical procedure.

* * * * *